(12) United States Patent
Johnson et al.

(10) Patent No.: US 7,112,439 B2
(45) Date of Patent: Sep. 26, 2006

(54) DUAL EXPRESSION VECTOR SYSTEM FOR ANTIBODY EXPRESSION IN BACTERIAL AND MAMMALIAN CELLS

(75) Inventors: Leslie Sydnor Johnson, Darnestown, MD (US); Ling Huang, Gaithersburg, MD (US)

(73) Assignee: MacroGenics, Inc., Rockville, MD (US)

( * ) Notice: Subject to any disclaimer, the term of this patent is extended or adjusted under 35 U.S.C. 154(b) by 0 days.

(21) Appl. No.: 10/753,309

(22) Filed: Jan. 8, 2004

(65) Prior Publication Data

US 2004/0197866 A1 Oct. 7, 2004

Related U.S. Application Data

(60) Provisional application No. 60/439,492, filed on Jan. 9, 2003.

(51) Int. Cl.
- *C12N 5/16* (2006.01)
- *C12N 15/85* (2006.01)
- *C12N 1/21* (2006.01)

(52) U.S. Cl. .................. 435/328; 435/320.1; 435/252.3

(58) Field of Classification Search ............. 435/320.1, 435/252.3, 252.33, 326, 366, 358, 328, 6
See application file for complete search history.

(56) References Cited

U.S. PATENT DOCUMENTS

| 4,703,004 A | 10/1987 | Hopp et al. |
| 5,506,121 A | 4/1996 | Skerra et al. |

OTHER PUBLICATIONS

Abrahmsen et al., "Secretion of heterologous gene products to the culture medium of *Escherichia coli*", Nucl. Acids Res. 14:7487-7500 (1986).
Amann et al., "Vectors bearing a hybrid trp-lac promoter useful for regulated expression of cloned genes in *Escherichia coli*", Gene 25:167-178 (1983).
Barbas et al., "Assembly of combinatorial antibody libraries on phage surfaces: the gene III site", Proc. Natl. Acad. Sci. USA 88:7978-7982 (1991).
Bennett et al., "Nucleotide sequence of region preceding trp mRNA initiation site and its role in promoter and operator function", Proc. Natl. Acad. Sci. USA 73:2351-2355 (1976).
Benoist and Chambon, "*In vivo* sequence requirements of the SV40 early promoter region", Nature 290:304-310 (1981).
Bird et al., "Single-chain antigen-binding proteins", Science 242:423-426 (1988).
Bornhorst and Falke, "Purification of proteins using polyhistidine affinity tags", Meth. Enzymol. 326:245-254 (2000).
Brinster et al., "Regulation of metallothionein—thymidine kinase fusion plasmids injected into mouse eggs", Nature 296:39-42 (1982).
Brizzard et al., "Immunoaffinity purification of FLAG® epitope-tagged bacterial alkaline phosphatase using a novel monoclonal antibody and peptide elution", BioTechniques 16:730-735 (1994).
Burks et al., "GenBank", Nucl. Acids Res. 19:2227-2230 (1991).
Carter et al., "Humanization of an anti-p185HER2 antibody for human cancer therapy", Proc. Natl. Acad. Sci. USA 89:4285-4289 (1992).
Chothia et al., "Structural determinants in the sequences of immunoglobulin variable domain", J. Mol. Biol. 278:457-479 (1998).
Clynes et al., "Inhibitory Fc receptors modulate in vivo cytoxicity against tumor targets", Nature Med. 6:443-446 (2000).
DeBoer et al., "The tac promoter: a functional hybrid derived from the trp lac promoters", Proc. Natl. Acad. Sci. USA 80:21-25 (1983).
Eikmanns et al., "A family of *Corynebacterium glutamicum/Escherichia coli* shuttle vectors for cloning, controlled gene expression, and promoter probing", Gene 102:93-98 (1991).
Evan et al., "Isolation of monoclonal antibodies specific for human c-myc proto-oncogene product", Mol. Cell. Biol. 5:3610-3616 (1985).
Friedrich and Soriano, "Promoter traps in embryonic stem cells: a genetic screen to identify and mutate developmental genes in mice", Genes Dev. 5:1513-1523 (1991).
Gardener et al., "The complete nucleotide sequence of an infectious clone of cauliflower mosiac virus by M13mp7 shotgun sequencing", Nucl. Acids Res. 9:2871-2878 (1981).
Geissendörfer and Hillen, "Regulated expression of heterologous genes in *Bacillus subtilis* using the Tn10 encoded tet regulatory elements", Appl. Microbiol. Biotechnol. 33:657-663 (1990).
Ghetie and Ward, Transcytosis and catabolism of antibody, Immunol. Res. 25:97-113 (2002).
Gilbert and Maxam, "The nucleotide sequence of the *lac* operator", Proc. Natl. Acad. Sci. USA 70:3581-3584 (1973).
Gilbert and Villa-Komaroff, "Useful proteins from recombinant bacteria", Scientific American 242:74-94 (1980).
Gossen and Bujard, "Tight control of gene expression in mammalian cells by tetracycline-responsive promoters", Proc. Natl. Acad. Sci. USA 89:5547-5551 (1992).
Hegedus et al., "A series of broad host range shuttle vectors for constitutive and inducible expression of heterologous proteins in insect cell lines" Gene 207:241-249 (1998).
Herrera-Estrella et al., "Expression of chimaeric genes transferred into plant cells using a Ti-plasmid-derived vector", Nature 303:209-213 (1983).

(Continued)

*Primary Examiner*—Nancy Vogel
(74) *Attorney, Agent, or Firm*—Jones Day

(57) ABSTRACT

The present invention provides a dual expression vector, and methods for its use, for the expression and secretion of a full-length polypeptide of interest in eukaryotic cells, and a soluble domain or fragment of the polypeptide in bacteria. When expressed in bacteria, transcription from a bacterial promoter within a first intron and termination at the stop codon in a second intron results in expression of a fragment of the polypeptide, e.g., a Fab fragment, whereas in mammalian cells, splicing removes the bacterial regulatory sequences located in the two introns and generates the mammalian signal sequence, allowing expression of the full-length polypeptide, e.g., IgG heavy or light chain polypeptide. The dual expression vector system of the invention can be used to select and screen for new monoclonal antibodies, as well as to optimize monoclonal antibodies for binding to antigenic molecules of interest.

27 Claims, 8 Drawing Sheets

OTHER PUBLICATIONS

Figure 1:
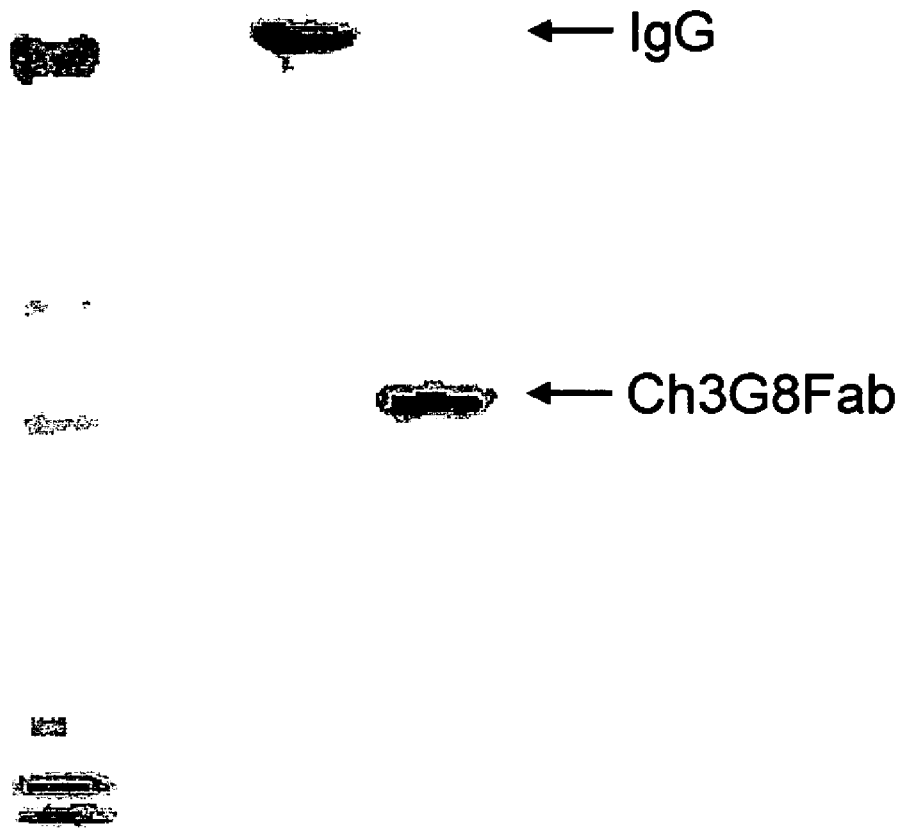

Herrera-Estrella et al., "Light-inducible and chloroplast-associated expression of a chimaeric gene introduced into *Nicotiana tabacum* using a Ti plasmid vector", Nature 310:115-120 (1984).

Hobom et al., "OmpA fusion proteins for presentation of foreign antigens on the bacterial outer membrane", Dev. Biol. Stand. 84:255-262.

Hoffman and Wright, "Fusions of secreted proteins to alkaline phosphatase: an approach for studying protein secretion" Proc. Natl. Acad. Sci. USA 82:5107-5111 (1985).

Hoogenboom et al., "Multi-subunit proteins on the surface of filamentous phage: methodologies for displaying antibody (Fab) heavy and light chains", Nucleic Acids Res. 19:4133-4137 (1991).

Horii et al., "Organization of the recA gene of *Escherichia coli*", Proc. Natl. Acad. Sci. USA 77:313-317 (1980).

Hudson and Kortt, "High avidity scFv multimers; diabodies and triabodies", J. Immunol. Meth. 231:177-189 (1999).

Huse et al., "Generation of a large combinatorial library of the immunoglobulin repertoire in phage lambda", Science 246:1275-1281 (1989).

Huse et al., "Generation of a large combinatorial library of the immunoglobulin repertoire in phage lambda. 1989", Biotechnology 24:517-523 (1992).

Huston et al., "Protein engineering of antibody binding sites: recovery of specific activity in an anti-digoxin single-chain Fv analogue produced in *Escherichia coli*", Proc. Natl. Acad. Sci. USA 85:5879-5883 (1988).

Johnson et al. , "Refolding, purification, and characterization of human erythropoietin binding protein produced in *Escherichia coli*", Protein Expr. Purif. 7:104-113 (1996).

Johnson et al., "Development of a humanized monoclonal antibody (MEDI-493) with potent in vitro and in vivo activity against respiratory syncytial virus", J. Infect. Dis. 176:1215-1224 (1997).

Jones et al., "Replacing the complementarity-determining regions in a human antibody with those from a mouse", Nature 321:522-525 (1986).

Kadonaga et al., "The role of the beta-lactamase signal sequence in the secretion of proteins of *Escherichia coli*", J. Biol. Chem. 259:2149-2154 (1984).

Kaiser et al., "Many random sequences functionally replace the secretion signal sequence of yeast invertase", Science 235:312-317 (1987).

Kang et al., "Linkage of recognition and replication functions by assembling combinatorial antibody Fab libraries along phage surfaces", Proc. Natl. Acad. USA 88:4363-4366 (1991).

Knappik and Plückthun, "An improved affinity tag based on the FLAG® peptide for the detection and purification of recombinant antibody fragments", BioTechniques 17:754-761 (1994).

Kozak, "Structural features in eukaryotic mRNAs that modulate the initiation of translation", J. Biol. Chem. 266:19867-19870 (1991).

Kutemeier et al., "Assembly of humanized antibody genes from synthetic oligonucleotides using a single-round PCR", BioTechniques 17:242-246 (1994).

Lo et al., "*Bacillus subtilis* beta-1,4-endoglucanase products from intact and truncated genes are secreted into the extracellular medium by *Escherichia coli*", Appl. Environ. Microbiol. 54:2287-2292 (1988).

MacIntyre et al., "Export incompatibility of N-terminal basic residues in a mature polypeptide of *Escherichia coli* can be alleviated by optimising the signal peptide", Mol. Gen. Genet. 221:466-474 (1990).

McCafferty et al., "Phage antibodies: filamentous phage displaying antibody antibody variable domains", Nature 348:552-554 (1990).

Morioka-Fujimoto et al., "Modified enterotoxin signal sequences increase secretion level of the recombinant human epidermal growth factor in *Escherichia coli*", J. Biol. Chem. 266:1728-1732 (1991).

Morrison et al., "Chimeric human antibody molecules: mouse antigen-binding domains with human constant region domains", Proc. Natl. Acad. Sci. USA 81:6851-6855 (1984).

Nakamura et al., "Use of a *lac* promoter-operator fragment as a transcriptional control switch for expression of the constitutive *lpp* gene in *Escherichia coli*", J. Mol. Appl. Gen. 1:289-299 (1982).

Nielsen et al., "A neural network method for identification of prokaryotic and eukaryotic signal peptides and prediction of their cleavage sites", Int. J. Neural Sys. 8:581-599 (1997).

Ochi et al., "Functional immunoglobulin M production after transfection of cloned immunoglobulin heavy and light chain genes into lymphoid cells", Proc. Natl. Acad. Sci. USA 80:6351-6355 (1983).

Oi et al., "Immunoglobulin gene expression in transformed lymphoid cells", Proc. Natl. Acad. Sci. USA 80:825-829 (1983).

Oka et al., "Synthesis and secretion of human epidermal growth factor by *Escherichia coli*", Proc. Natl. Acad. Sci. USA 82:7212-7216 (1985).

Petrenko et al., "Expression vector with two-step control by the $cl\text{-}p_R\text{-}Q\text{-}p'_R\text{-}qut\text{-}t'_R$ module of coliphage lambda", Gene 78:85-91 (1989).

Pirotta, "Sequence of the $O_R$ operator of phage λ", Nature 254:114-117 (1975).

Queen et al., "A humanized antibody that binds to the interleukin 2 receptor",Proc. Natl. Acad. USA 86:10029-10033 (1989).

Ravtech and Bolland, "IgG Fc receptors", Annu. Rev. Immunol. 19:275-290 (2001).

Reese et al., "Improved splice site detection in Genie", J. Comput. Biol. 4:311-323 (1997).

Reff et al., "Depletion of B cells in vivo by a chimeric mouse human monoclonal antibody to CD20", Blood 83:435-445 (1994).

Schier et al., "Isolation of picomolar affinity anti-c-erbB-2 single-chain Fv by molecular evolution of the complementarity determining regions in the center of the antibody binding site", J. Mol. Biol. 263:551-567 (1996).

Schleif, "Regulation of the L-arabinose operon of *Escherichia coli*", Trends Genet. 16:559-565 (2000).

Skerra and Pluckthun, "Assembly of a functional immunoglobulin Fv fragment in *Escherichia coli*", Science 240:1038-1041 (1988).

Skerra and Schmidt, "Applications of a peptide ligand for streptavidin: the Strep-tag", Biomol. Eng. 16:79-86 (1999).

Skerra et al., "Use of the Strep-Tag and streptavidin for detection and purification of recombinant proteins", Meth. Enzymol. 326:271-304 (2000).

Tao et al., "Structural features of human immunoglobulin G that determine isotype-specific differences in the complement activation", J. Exp. Med. 178:661-667 (1993).

Villa-Komaroff et al., "A bacterial clone synthesizing proinsulin", Proc. Natl. Acad. Sci. USA 75:3727-3731 (1978).

Wagner et al., "Nucleotide sequence of the thymidine kinase gene of herpes simplex virus type 1", Proc. Natl. Acad. Sci. USA 78:1441-1445 (1981).

Warne et al., "Use of a modified *Escherichia coli trpR* gene to obtain tight regulation of high-copy-number expression vectors", Gene 46:103-112.

Wang et al., "BTag: a novel six-residue epitope tag for surveillance and purification of recombinant proteins", Gene 169:53-58 (1996).

Wilson et al., "The structure of an antigenetic determinant in a protein", Cell 37:767-778 (1984).

Wu et al., "Stepwise in vitro affinity maturation of Vitaxin, an alphav beta3-specific humanized mAb", Proc. Natl. Acad. Sci. USA 95:6037-6042 (1998).

Yamamoto et al., "Identification of a functional promoter in the long terminal repeat of Rous sarcoma virus", Cell 22:787-797 (1980).

```
      -19              -15                    -10                      -5
Met Gly Trp Ser Cys Ile Ile Leu Phe Leu Val Ala Thr Ala Thr
ATG GGA TGG AGC TGT ATC ATC CTC TTC TTG GTA GCA ACA GCT ACA
              Mammalian Signal Peptide (mSigP)
G⟨GTAAGGGGCTCACAGTAGCAGGCTTGAGGTCTGGACATATATATGGGTGACAAGATC TCGCAACGCAATTAATGTGAGTTAGCTCACTCATTAGGCACCCCAGGCTTTACACTTTA
                                                 lacPO            -35
TGCTTCCGGCTCGTATGTTGTGTGGAATTGTGAGCGGATAACAATTTCTAGAAATAATT
           -10
TTGTTTAACTTTAAGAAGGAGATATACAT
                 RBS
Met Lys Tyr Leu Leu Pro Thr Ala Ala Ile Gly Leu Leu Leu Leu
ATG AAA TAC CTG CTG CCG ACC GCT GCG ATC GGT CTC CTT CTC CTC
              Bacterial Signal Peptide (bSigP)

Leu Leu Thr   Gly Val His Ala Gln Val Thr Leu Arg
CTC CTC ACA   G⟵GT GTC CAC GCA CAG GTT ACC CTG AGA...
              -1 +1             VH
```

FIG. 4A

```
Asp Lys Arg Val gly glu arg pro ala
GAC AAG AGA GTT G⟨GT GAG AGG CCA GCA  ...
      CH1              intron
Asp Lys Arg Val gly glu arg pro Stop
GAC AAG AGA GTT G⟨GT GAG AGG CCA TAA ...
```

⟨ ⇐ mRNA splicing sites

FIG. 4B

DUAL EXPRESSION VECTOR SYSTEM FOR ANTIBODY EXPRESSION IN BACTERIAL AND MAMMALIAN CELLS

This application claims the benefit of priority under 35 U.S.C. § 119(e) to provisional application No. 60/439,492, filed Jan. 9, 2003, which is incorporated by reference herein in its entirety.

1. FIELD OF THE INVENTION

The present invention provides a dual expression vector, and methods for its use, for the expression and secretion of Fab fragments in bacteria and corresponding full length IgG in mammalian cells. The vector comprises a regulatory and coding sequences for a polypeptide of interest, e.g., a heavy or light chain of an IgG, wherein a bacterial promoter and signal sequence are included within a first intron located within the signal sequence of the polypeptide, e.g., an IgG heavy or light chain gene, and, when the protein of interest has more than one intron, e.g., an Ig heavy chain, a bacterial stop codon is included within a second intron, e.g., the intron between the CH1 domain and the hinge region of the heavy chain gene. The vector also comprises a mammalian promoter, origins of replication for both bacterial and mammalian cells, and optionally, one or more selectable markers. Thus, when expressed in bacteria, transcription from the bacterial promoter and termination at the stop codon in the second intron results in expression of a fragment of the polypeptide, e.g., a Fab fragment, whereas in mammalian cells splicing removes the bacterial regulatory sequences located in the introns and generates the mammalian signal sequence, allowing expression of the full-length polypeptide, e.g., IgG heavy or light chain polypeptide. The dual expression vector system can be used to select and screen for new monoclonal antibodies, as well as to optimize monoclonal antibodies for binding to antigenic molecules of interest. Using this system, initial screening or selection steps can be accomplished by expressing Fab (or scFv) in *E. coli*, and the resulting Fab binding molecules can be readily expressed as bivalent IgG molecules of the desired isotype for functional testing.

2. BACKGROUND OF THE INVENTION

Recombinant expression systems have been key to the development of current antibody engineering technology. The demonstration of coexpression of cloned light and heavy chain genes of an IgM or an IgG in mammalian cells led rapidly to the generation and testing of chimeric Mabs containing human constant regions (Ochi et al., 1983, Proc. Natl. Acad. Sci. U.S.A. 80:6351 6355; Oi et al., 1983, Proc. Natl. Acad. Sci. U.S.A. 80:825 829; Morrison et al., 1984, Proc. Natl. Acad. Sci. U.S.A. 81(21):6851–5); Subsequently, methods were developed to introduce human sequences into the variable regions of mouse immunoglobulins without reducing avidity, resulting in antibodies with very low potential immunogenicity in human subjects (Jones et al., 1986, Nature 321:522 525; Queen et al., 1989, Proc. Natl. Acad. Sci. U.S.A. 86:10029 10033). Reproducible methods have been developed to express large amounts of such recombinant antibodies in CHO or mouse myeloma cells for the preparation of highly purified material for human testing and eventual sale. There are now a number of such Mabs which have been approved and marketed for human use, including Rituxan and Herceptin for cancer treatment, Synagis for the prevention of RSV infection, Remicade for treatment of rhumatoid arthritis, and Zenapax for prevention of graft rejection (Reff et al., 1994, Blood 83:435 445; Carter et al., 1992, Proc. Natl. Acad. Sci. U.S.A. 89(10):4285–9; Johnson et al., 1997, J. Infect. Dis. 176:1215 1224; Queen et al., 1989, Proc. Natl. Acad. Sci. U.S.A 86:10029 10033; see Table 1).

Likewise, the demonstration that Fv, single chain Fv, or Fab molecules could be successfully expressed in microbial systems led rapidly to the development of methods to utilize this expression technology to exploit diverse libraries of VH and VL sequences (Skerra et al., 1988, Science 240:1038 1041; Bird et al., 1988; Science 242:423 426; Huston et al., 1988, Proc. Natl. Acad. Sci. U.S.A 85:5879 5883). Combinatorial libraries of VL and VH sequences were initially expressed from bacteriophage lambda and the binding of a particular combination to antigen screened using a plaque lift assay (Huse et al., 1989, Science 246:1275–81; Huse et al., 1992, Biotechnology 24:517 523). By tethering either an scFv or Fab on the surface of a filamentous bacteriophage it was possible to select for binding phage containing the genes for the binding regions in their genome using panning techniques (McCafferty et al., 1990, Nature 348:552 554; Hoogenboom et al., 1991, 19: 4133 4137; Bird et al., 1988, Science 242:423 426; Kang et al., 1991, Proc. Natl. Acad. Sci. U.S.A. 88:4363 4366). The ability to select rather than screen allowed the enormous diversity contained in large libraries of 109 or greater individual members to be exploited to identify and isolate rare binders. Thus, it is now possible to isolate antibody fragments binding with reasonable affinity to almost any proteinaceous antigen from a large diverse bacteriophage library. Methods have also been developed to improve the affinity of antibody fragments by iterative rounds of mutagenesis of the CDRs and screening or selecting for improved binding to antigen (Schier et al., 1996, J. Mol. Biol. 263: 551 567; Wu et al., 1998, Proc. Natl. Acad. Sci. U.S.A. 95:6037 6042).

Despite breakthroughs in using Fab or scFv expression systems for the identification and affinity maturation of novel specificities, full length IgG molecules offer several advantages. One of the key features of an IgG is its bivalent structure. Cooperativity between the two Fab arms of an IgG in binding to antigen leads to a higher avidity of a bivalent IgG compared to the monovalent Fab. The degree of difference between the affinity of the individual Fab arms and the avidity of the IgG is most pronounced when the antigen is also multivalent or surface bound. The amount of cooperativity is more pronounced when the antigen is present at higher density and less pronounced in Mab with high affinity Fab arms. In practical terms, this means that above a certain antigen density threshold a Mab with high affinity but low cooperativity will have the same avidity as a Mab having Fab arms with moderate affinity but high cooperativity. This latter Mab would be more selective for areas of high antigen density compared to the former Mab. One can envision instances where either Mab would be advantageous. For instance, there are very few true cancer antigens, i.e., antigens which are expressed only on tumor cells. Most are expressed on tumor cells at a higher density, but are expressed on other cell types as well. Thus, a Mab with high avidity but moderate affinity might be more selective for tumor than for normal cells expressing the antigen at a lower density. Likewise, during viral infection, antigen may be present on the virus, on virally infected cells, and secreted in free form. A neutralizing Mab selective for areas of higher antigen density could target the virus and infected cells rather than free antigen, or other areas of low antigen density, and thus might have equal or better efficacy compared to a high affinity Mab. Methods have been developed to select for higher avidity fragments using various strategies to link monomers of Fab or scFv (Hudson et al., 1999, J. Immunol. Methods 231:177 189). These constructs are useful but may not accurately replicate the avidity provided by linking Fab arms using an Fc. Additionally, one may want to first identify specific binders and then those which have higher cooperativity. For instance, in the example above, one might want to screen for viral neutralization but find that most monovalent Fabs had little activity. Converting to full length IgG might allow selection for neutralizing activity due to increased avidity.

In other cases, effector function may be required for optimal potency of the binding molecule. The interaction between the Fc portion of immunoglobulin molecules and specific cell surface receptors allows the coupling of antigen binding to effector cell functions.

There are three classes of Fc receptors for IgG present in humans and rodents, which are designated RI, RII, and RIII (Ravetch and Bolland, 2001, Annu. Rev. Immunol. 19: 275 290). RI, present on monocytes and macrophages, binds to monomeric IgG with high affinity. RII is present on a wide variety of cells including B cells, platelets, neutrophils, macrophages and monocytes, and binds to multimeric IgG (immune complexes or aggregated IgG) with moderate affinity. Two forms of RII are expressed, differing by the presence of either an activation (ITAM) RIIa domain or an inhibitory (ITIM) RIIb domain on the intracellular portion of the receptor. The relative level of activating and inhibitory receptors on a given cell determines the response to immune complexes. B cells express only the inhibitory form. RIII, like RII, binds to multimeric IgG (immune complexes or aggregated IgG) with moderate affinity. There are also two forms of RIII. The ITAM domain on the associated gamma chain mediates signaling through RI, as well as through RIIIa and the FcE receptors. The signaling molecule RIIa associates with the ITAM containing gamma chain on NK, monocytes, macrophages, and certain T cells. On NK cells, signaling by RIIa also involves the TCR zeta chain. RIIIb is a non signaling form and is expressed on (human) neutrophils as a GPI linked molecule.

In the body, RI sites are generally occupied by monomeric IgG while RII and RIII receptors are unoccupied and available to interact with immune complexes. Cross linking of activating Fc receptors by antibody antigen complexes can result in the phagocytosis of pathogens, killing of foreign and transformed cells by direct cytotoxicity, the clearance of toxic substances, and the initiation of an inflammatory response. Additionally, the Fc contains sites for interacting with complement components (Tao et al., 1993, J Exp Med 178:661 667). Finally, the Fc is responsible for the long half-life in vivo of IgGs through a specific interaction with the MHC related FcRn receptor (Ghetie and Ward, 2002, Immunol Res. 25:97 113).

Clearly, in instances where the target is a bacterium or a cancerous cell, it would be advantageous to test agents for clearance or killing rather than only binding. In that case, an IgG would be the preferred molecule to test. For instance, the chimeric anti CD20 Mab Rituxan was selected based on its having strong ADCC activity against human B cells (Reff et al., 1994, Blood 83:435 445). Additionally, although the anti HER2 antibody Herceptin binds to and blocks signaling through an EGF like receptor on tumor cells, recent studies have indicated that tumor protection is largely Fc-mediated (Clynes et al., 2000, Nat. Med. 6:443 446).

There is a great interest in expression, selection and improvement of antibodies using scFv or Fab systems. Using the technologies currently available, however, the resulting scFv or Fab fragments must be re-cloned into a vector for expression of the full length glycosylated Mab for further testing and development. This step severely limits the number of Mabs which can be tested at this stage. Thus, despite such interest in the technology, as yet, no effective system for selecting and improving full length Mab molecules useful for human therapeutics has been developed.

Citation or discussion of a reference herein shall not be construed as an admission that such is prior art to the present invention.

3. SUMMARY OF THE INVENTION

The present invention provides a vector system, and methods for its use, for the selection, screening and expression of optimized monoclonal antibodies. The vector system can be used to express and select for Fab fragments in bacteria, preferably *E. coli*, and corresponding full length antibodies (e.g., IgGs) in eukaryotic cells, preferably mammalian cells. Using this system, screening and/or selection of the initial binding molecules can be accomplished using *E. coli* expressed Fab or scFv, and the resulting binding molecules can be quickly expressed as bivalent antibodies of the desired isotype for functional testing.

The invention is based, in part, on the Applicants' discovery and development of a dual expression vector system capable of expressing and secreting into the periplasmic space antibody fragments in bacteria and expressing and secreting full-length IgG in mammalian cells. In this novel vector, regulatory elements required for expression and secretion of Fab fragments in bacteria overlap sequence elements required for both proper processing of IgG heavy and light chain RNA transcripts and secretion of IgG heavy and light chain polypeptides in mammalian cells. In particular, a bacterial promoter and signal sequence are included in an intron located within the sequence coding for the signal sequence of a mammalian IgG heavy or light chain gene, and a bacterial stop codon is included in another intron between the CH1 and the hinge region of the heavy chain gene (or, in an alternative embodiment in an intron located between the hinge region and the CH2 domain). Thus, when expressed in bacteria, transcription from the bacterial promoter and termination at the stop codon in the second intron results in Fab fragment expression in bacteria periplasmic space, whereas in mammalian cells, splicing removes the bacterial promoter and signal sequence and regenerates the mammalian signal sequence, allowing expression of the full-length IgG heavy or light chain polypeptide. An important feature of the vector is the structural and functional overlap of a bacterial and mammalian regulatory sequence elements, i.e., the mammalian signal sequence and splice acceptor site, and the bacterial promoter and signal sequences, so that the functionality of all four of these sequence elements is maintained. It is therefore critical in construction of the vector that any changes made within this overlap region maintain the functionality of these four sequence elements.

This improved system enhances and streamlines the identification of the best functional Mabs for use as therapeutic agents. When expressed in bacterial cells, the bacterial promoter controls expression of the Fab (or scFv), allowing selection and screening for antigen binding in the bacterial cells. However, when expressed in mammalian cells, splicing results in removal of the introns within the mammalian signal sequence and between the CH1 and hinge region of the heavy chain, and hence the bacterial promoter, bacterial signal sequence, and stop codon are removed, and the mammalian signal sequence reconstructed. A mammalian promoter, e.g., CMV promoter, is located 5' of start site of the mammalian signal sequence, directing transcription of a nucleotide sequence encoding the heavy chain or light chain of the IgG molecule, and thus, the full-length heavy chain or light chain IgG molecule is expressed in the mammalian cell.

In one embodiment, the invention encompasses a vector for expression of a heavy chain or light chain of an IgG in mammalian cells and a Fab fragment portion of a heavy chain or light chain in bacteria, said vector comprising: (a) a bacterial origin of replication, (b) a mammalian origin of replication, and (c) a mammalian promoter for expression in cells, said vector being operatively associated with a nucleotide sequence encoding said heavy chain or said light chain, said nucleotide sequence comprising: (i) a mammalian signal sequence comprising a first intron, said first intron comprising a bacterial promoter and a bacterial signal sequence operatively associated with a sequence encoding the Fab domain of said heavy chain or said light chain, such that said bacterial promoter and signal sequence direct expression and secretion into the periplasmic space of said Fab fragment of said heavy chain or said light chain in a bacterial cell and said mammalian promoter and signal sequence direct expression and secretion in a mammalian cell of said heavy chain or said light chain; and (ii) when said vector encodes said heavy chain, a second intron is included between the CH1 and the hinge region of said heavy chain sequence, said second intron comprising a stop codon, preferably, close to the 5' end of the intron, such that translation in bacteria ends after said hinge region sequence. In another embodiment, the invention provides the vector described above wherein the bacterial promoter comprises a lacPO sequence. In a specific embodiment, the invention provides such a vector wherein the bacterial signal sequence is a pelB signal sequence. In another specific embodiment, the invention provides the vector described above wherein the light chain sequence is genetically modified to comprise sequence encoding an epitope tag or affinity label. In yet another embodiment, the invention provides the vector described above wherein the epitope tag an HSV tag at the C-terminal of the Fd chain. In another embodiment, the affinity tag of the vector is a hexahistidine tag at the C-terminal of the Fd chain.

In another specific embodiment, the vector comprises sequences encoding both a heavy chain and a light chain, each operably linked to mammalian and bacterial promoters and signal sequences. In another specific embodiment, the heavy chain or light chain is a chimeric heavy chain or light chain. In yet another specific embodiment, the heavy chain or light chain sequence is a human or humanized heavy chain or light chain sequence.

In another embodiment, the invention provides a bacterial cell comprising the vector, as described above. In a specific embodiment, the bacterial cell is an E. coli cell.

In another specific embodiment, the invention provides a mammalian cell comprising the vector described above. In a specific embodiment, the mammalian cell is a human or murine cell, preferably, a myeloma cell, a CHO cell, HEK cell, a NSO cell, a NS1 cell, a BHK cell, a COS cell, a 293 cell, or a 3T3 cell.

In another specific embodiment, the invention provides a cell comprising a vector described above which expresses both the heavy chain and light chain. In another specific embodiment of this aspect of the invention, the heavy chain and light chains are expressed in the same cell from different vectors, at least one (and preferably both) of which is the vector described above.

In another embodiment, the invention provides a vector for expression of IgG in mammalian cells and Fab fragments in E. coli comprising a nucleotide sequence encoding a Fd (VH CH1) segment of an IgG heavy chain or light chain operatively linked to (preferably fused to) sequences encoding a filamentous phage gene VIII or gene III protein coding region such that, when the vector is expressed in a bacterial cell, an Fd gene VIII or Fd gene III fusion is produced. In another embodiment, the vector contains the nucleotide sequence encoding the complementary heavy chain gene or light chain gene, which is not operatively linked to phage sequences.

In another aspect of the invention, a method for identifying Mabs for use as therapeutic agents is provided. This method comprises: (a) providing a control cell comprising a vector for expression of IgG in mammalian cells and Fab fragments in E. coli encoding a control IgG; (a) contacting a library of test cells with an antigen, wherein each test cell expresses a vector for expression of IgG in mammalian cells and Fab fragments in E. coli encoding a IgG genetically modified relative to the control IgG; (c) measuring the binding affinity of periplasmic extracts of a test cell and said antigen relative to the binding affinity of periplasmic extracts of the control cell and said antigen, such that if the binding affinity of the periplasmic extracts of the test cell and said antigen is greater than the binding affinity of the periplasmic extracts of the control cell and said antigen, then a cell expressing a Mab useful as a therapeutic is identified. In a specific embodiment of this method, the method further comprises, after step (c), the steps of: (d) expressing in a mammalian cell the vector isolated from the test cell of step (c); (e) contacting the mammalian cell with said antigen; and (f) measuring the binding affinity of the genetically modified IgG expressed in the mammalian cell relative to the binding affinity of the control IgG.

In another aspect of the invention, a phage display screening method for identifying Mabs for use as therapeutic agents is provided. This method comprises: (a) providing a bacterial cell expressing a control phage encoding a fd-filamentous phage-gene III or fd-filamentous phage-gene VIII fusion; (b) contacting a member of a phage library, said library comprising a plurality of test cells producing test phage encoding a light chain and an fd (VH CH1)-gene III or an fd (VH CH1)-gene VIII fusion, which have been modified relative to the control phage, with an antigen; (c) measuring the binding affinity of a test phage and said antigen relative to the binding affinity of the control phage and said antigen, such that if the binding affinity of the test phage and said antigen is greater than the binding affinity of the control phage and said antigen, then a cell expressing a Mab useful as a therapeutic is identified. In a specific embodiment of this method, the method further comprises, after step (c), the steps of: (d) expressing in a mammalian cell the vector isolated from the test cell of step (c); (e) contacting the mammalian cell with said antigen; and (f) measuring the binding affinity of the genetically modified IgG expressed in the mammalian cell relative to the binding affinity of the control IgG.

The present invention also provides a composition comprising a plurality of bacterial cells expressing Fab polypeptides comprising the vector for expression of IgG in mammalian cells and Fab fragments in E. coli.

In addition, the present invention also provides a composition comprising a plurality of bacterial cells comprising the vector for expression of IgG in mammalian cells and Fab fragments in *E. coli* and filamentous phage expressing Fab polypeptides. In specific embodiments, the bacterial cells are *E. coli* cells, and the filamentous phage is an fd phage.

In another embodiment, the invention further encompasses production of cocktails of Mabs which are particularly useful for rapid development of passive therapeutics to multiple targets. The vectors described herein may be used to make libraries of Fab expressing *E. coli* and phage from naïve and immunized human subjects in order to isolate clinically relevant Mabs.

In addition, the principles used in designing the vectors for expression of Fab fragments in bacteria and full-length IgGs in mammalian cells can be applied to create vectors for expression of a portion of a particular protein in bacteria and the full length protein in mammalian cells. For example, the invention provides a vector for expression of a secreted or membrane-bound polypeptide in mammalian cells and a soluble fragment of said polypeptide in bacteria, said vector comprising: (a) a bacterial origin of replication, (b) a mammalian origin of replication, and (c) a mammalian promoter operatively associated with a nucleotide sequence encoding said secreted or membrane-bound polypeptide, said nucleotide sequence comprising a mammalian signal sequence comprising at least one intron, said intron comprising a bacterial promoter and a bacterial signal sequence operatively associated with a sequence encoding said soluble domain of said polypeptide, such that said bacterial promoter and bacterial signal sequence direct expression and secretion of said soluble domain of said polypeptide into the periplasmic space in a bacterial cell and said mammalian promoter and said mammalian signal sequence directs expression and secretion of said polypeptide in mammalian cells, wherein said mammalian promoter is operatively associated with said nucleotide sequence encoding said soluble domain of said polypeptide.

As used herein, the terms "antibody" and "antibodies" refer to monoclonal antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies of interest), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

As used herein, the term "dual expression vector system" refers to a vector system for expression of a polypeptide of interest in eukaryotic cells, preferably mammalian cells, and for expression of a fragment of the polypeptide of interest into the periplasmic space in bacterial cells. In a preferred embodiment, the polypeptide of interest is an antibody chain, and the fragment or domain is a Fab fragment or an scFv fragment. Most preferably, the polypeptide of interest is the heavy chain or light chain of an IgG, and the Fab fragment of an IgG. Therefore, the terms "antibody dual expression vector system" and "IgG dual expression vector system" are also referred to herein.

As used herein, the terms "dual expression vector cassette" or "dual expression vector polynucleotide cassette", used interchangeably herein, refer to a polynucleotide comprising the coding sequences of a polypeptide of interest and regulatory sequences required for expression and secretion of the polypeptide of interest in eukaryotic cells, preferably mammalian cells, and for expression and secretion of a fragment or domain of the polypeptide of interest into the periplasmic space in bacterial cells. Such regulatory sequences comprise an intron within a eukaryotic signal sequence, preferably a mammalian, signal sequence, which includes, within the intron, a bacterial promoter and a bacterial signal sequence, positioned in a particular fashion, as described in detail herein, to allow expression and secretion of the polypeptide of interest in eukaryotic cells, preferably mammalian cells, and expression and secretion of a fragment or domain of the polypeptide of interest (as determined positioning a stop codon in a second intron of the sequence encoding the polypeptide of interest) into the periplasmic space in bacterial cells. The term "antibody expression vector polynucleotide cassette" refers to a preferred embodiment of the invention wherein the polypeptide of interest is an antibody chain, and the fragment or domain is a Fab fragment or an scFv fragment. Likewise, the term "IgG expression vector polynucleotide cassette" refers to a specific embodiment wherein the polypeptide of interest is the heavy chain or light chain of an IgG, and the Fab fragment of an IgG.

These and other aspects of the present invention will be better appreciated by reference to the following Figures and Detailed Description.

4. BRIEF DESCRIPTION OF THE FIGURES

FIG. 1. Coomassie Blue staining of purified Ch3G8Fab (pMGX513) in non reducing condition. Lane 1: protein standard (SeeBlue®Plus Stained; Invitrogen); Lane 2: human IgG (control); Lane 3: ch3G8Fab.

Figure 2:
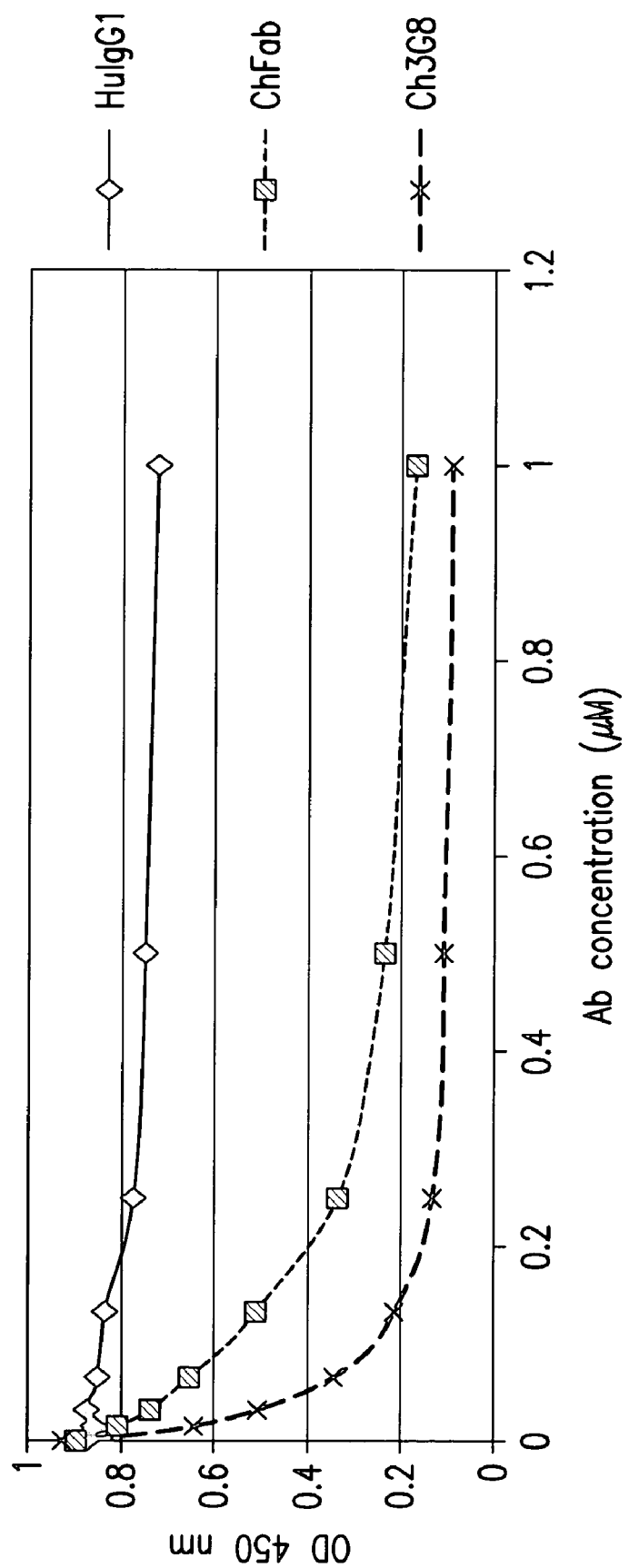

FIG. 2. Inhibition of sCD16-Ig binding to immune complexes. 1) HuIgG1, human IgG1, i.e., Ch4 4 20 (as negative control); 2) ChFab; 3) Ch3G8 (IgG1).

Figure 3:
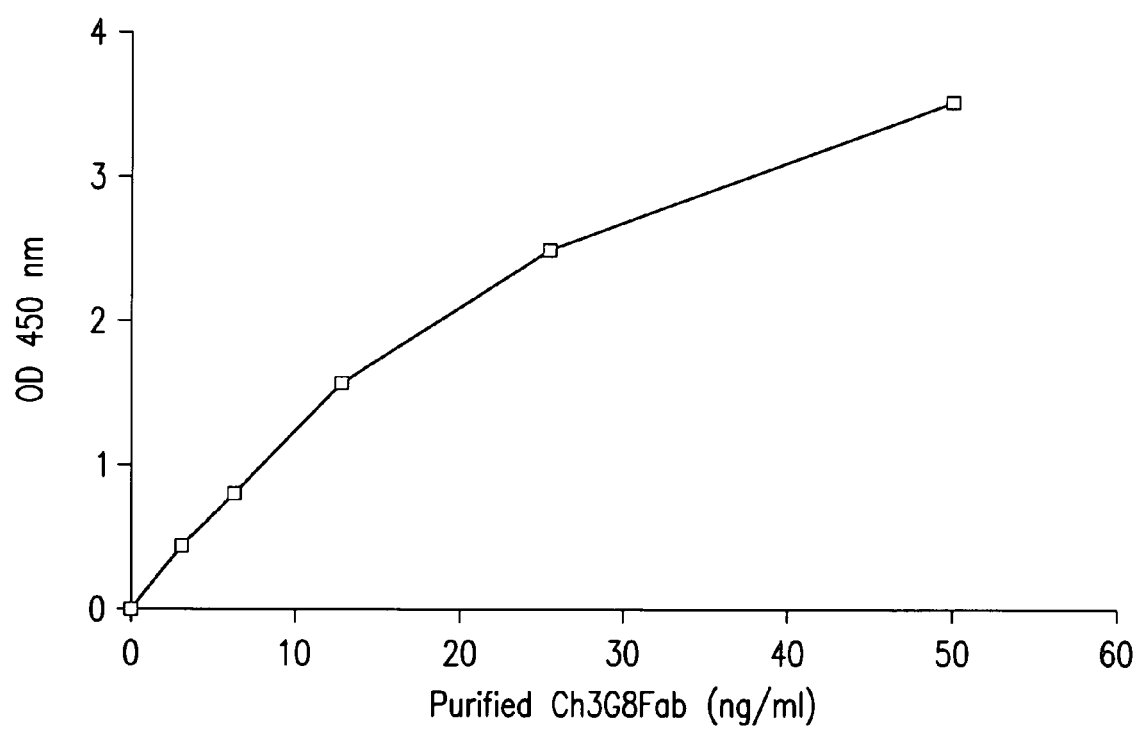

FIG. 3. Binding of ch3G8Fab to sCD16A.

FIGS. 4A and B. Design of intron sequences. A. Placement of lac promoter and bacterial signal sequence in an intron in the mammalian signal peptide coding sequence (SEQ ID NOs 6, 7, and 8). B. Placement of TAA stop codon in CH1 Hinge intron (SEQ ID NOs 9–12).

Figure 5:
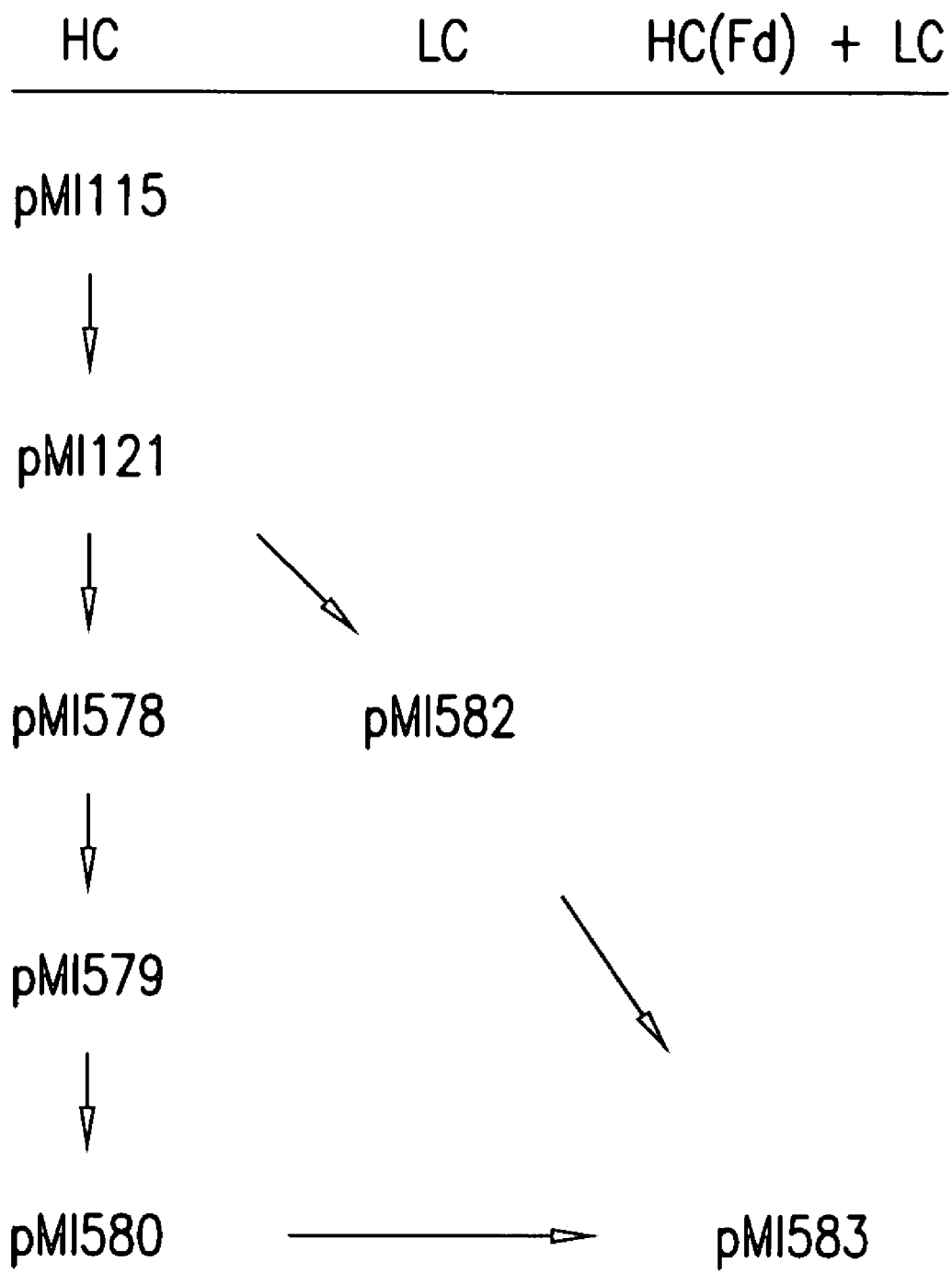

FIG. 5. Construction and nomenclature of heavy chain (HC) and light chain (LC) expression plasmids.

Figure 6:
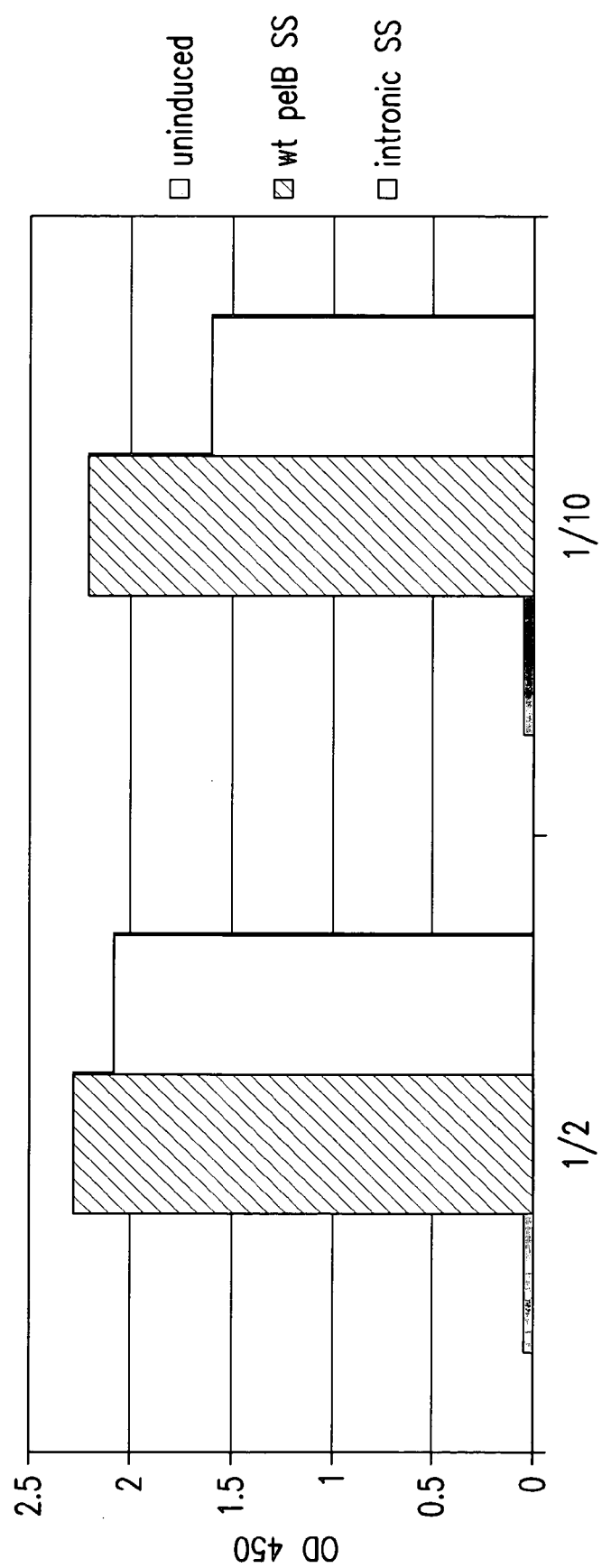

FIG. 6. Detection of Chimeric LC in *E. coli* Periplasmic Extracts.

Figure 7:
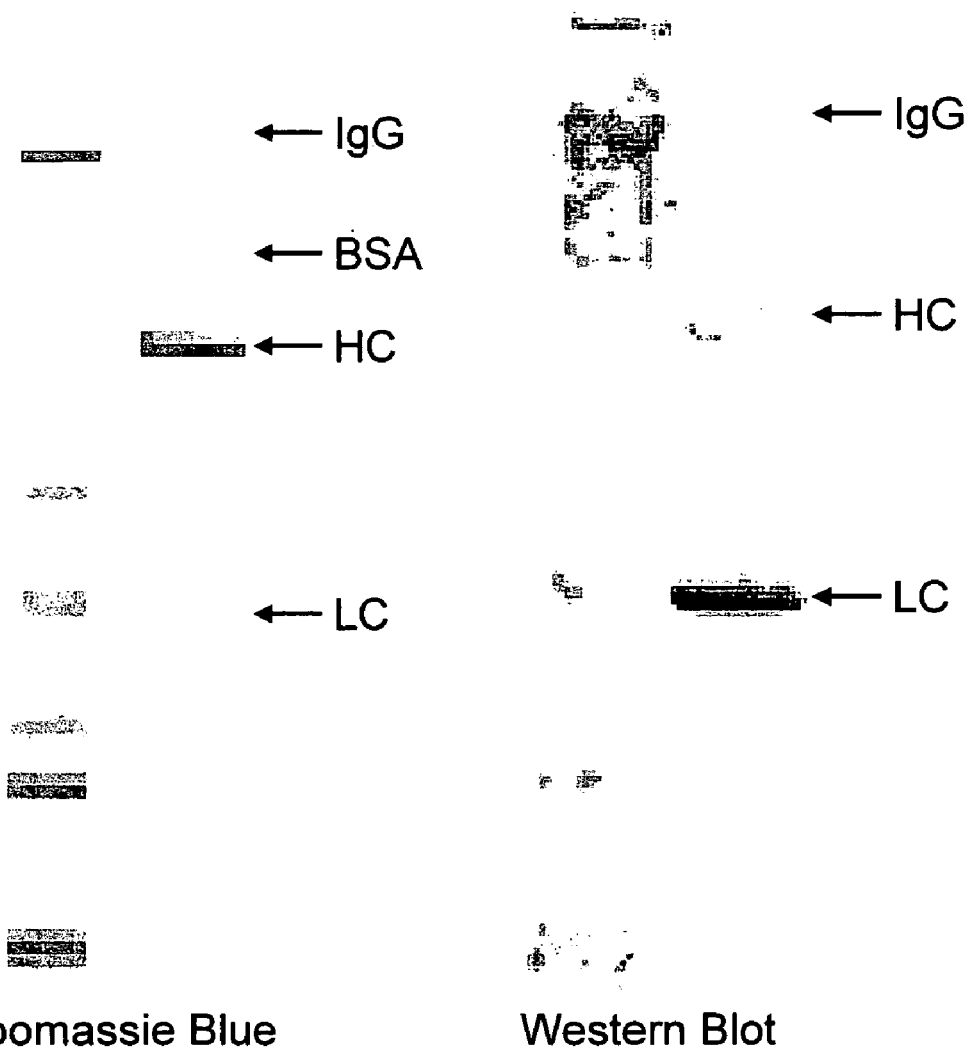

FIG. 7. Coomassie Blue and Western Blot of purified IgG expressed from pMFX583.

Figure 8:
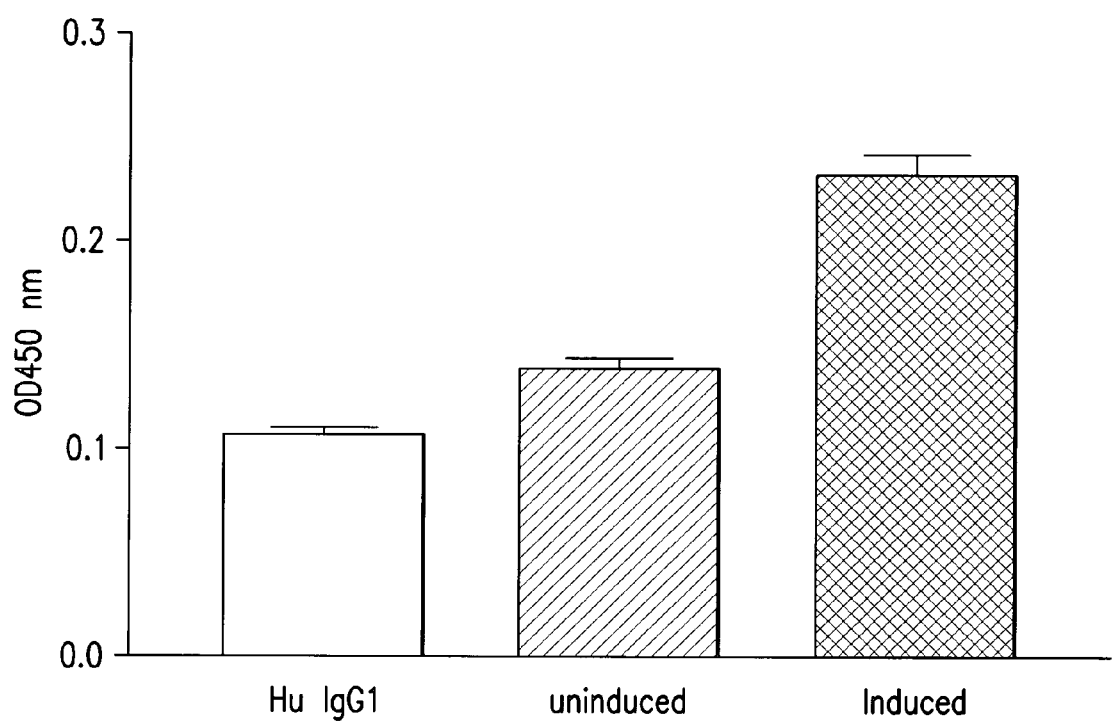

FIG. 8. Binding of Hu3G8 Fab from pMGX583 from periplasmic extracts to sCD16A measured by anti CD16 ELISA.

5. DETAILED DESCRIPTION OF THE PREFERRED EMBODIMENT

The present invention is directed to a novel dual expression vector system for expression and secretion of Fab fragments in bacterial cells, e.g., *E. coli* cells, and for expression of IgG heavy and light chain polypeptides in eukaryotic cells, preferably mammalian cells, but also, e.g., insect cells or avian cells, and to methods for its use in screening and optimization of monoclonal antibodies with particular binding characteristics. As discussed above, the invention is based, in part, on the Applicants' development of a dual expression vector system capable of expressing and secreting into the periplasmic space antibody fragments in bacteria and expressing and secreting full-length antibodies in mammalian cells. In this novel vector a bacterial promoter and signal sequence are included in an intron located within the signal sequence of a mammalian IgG heavy or light chain gene, and a bacterial stop codon is included in another intron between the CH1 and the hinge region of the heavy chain gene. Thus, when expressed in bacteria, transcription from the bacterial promoter and termination at the stop codon in the second intron results in Fab fragment expression, whereas in mammalian cells, splicing removes the bacterial control elements and regenerates the mammalian signal sequence, allowing expression of the full-length IgG heavy or light chain polypeptide. Thus, this dual purpose vector is designed to maintain the structure and function of the bacterial and mammalian regulatory sequence elements, i.e., the mammalian signal sequence and splice acceptor site, and the bacterial promoter and signal sequences.

Described below, are compositions and methods relating to the construction and use of the novel dual expression vector system. In particular, Section 5.1 describes compositions of the invention, including DNA cassettes designed for dual expression of a polypeptide of interest in a eukaryotic cell and a fragment thereof in bacteria, vectors comprising the dual expression vector polynucleotide cassette, host cells comprising such cassettes and vectors, and kits comprising such cassettes, vectors, and host cells. Sections 5.2 and 5.3 describe methods for use of the invention, including methods for use of the novel vector sequence for identifying novel antibodies, and for selection and screening of optimized monoclonal antibodies in both eukaryotic and bacterial systems, as well as generalized methods for applying these principles to construct a dual expression vector system for any membrane-bound or secreted protein of interest.

5.1 The Dual Expression Vector

The dual expression vector system having the sequence and functional elements outlined above may be constructed using a variety of techniques available in the art. In a preferred embodiment, the vector comprises: (1) a mammalian promoter; (2) a nucleotide sequence encoding an IgG heavy chain or light chain; said nucleotide sequence comprising: (a) a mammalian signal sequence comprising: (i) a first intron, said first intron comprising a bacterial promoter and signal sequence, such that the bacterial promoter and signal sequence overlap a first splice acceptor site and are operably linked to the IgG heavy or light chain coding sequence such that said bacterial promoter and signal sequence direct expression and secretion into the periplasmic space of said Fab domain of said heavy chain or said light chain in a bacterial cell and said mammalian promoter and signal sequence directs expression and secretion of said heavy chain or said light chain in a mammalian cell; and (ii) when said vector encodes said heavy chain, a second intron between sequence encoding the CH1 and the hinge region of the heavy chain gene, said second intron comprising a bacterial stop codon; (3) a bacterial origin of replication; (4) and a mammalian origin of replication. In addition to the foregoing sequence elements, the vector may further comprise selectable markers for cloning and growth of the vector in bacterial cells, and for growth and selection of cells bearing the vector in both bacterial and eukaryotic cells, multiple cloning site sequences for addition of other nucleotide sequences, as well as other sequences of interest. The sequence elements are described in detail hereinbelow.

5.1.1 Dual Expression Vector Cassette Sequences

The nucleotide sequence encoding a polypeptide of interest, e.g., an IgG heavy chain or light chain, is designed with a mammalian signal sequence which comprises a first intron, and if the sequence encodes a heavy chain, a CH1-hinge region comprising a second intron. The first and second introns are designed to include bacterial regulatory sequences which direct expression and secretion of the polypeptide in bacterial cells, and which are removed by splicing when the dual expression vector is expressed in mammalian cells. The particular sequence composition and structure of the dual expression vector cassette is described in detail herein.

The first intron is designed to be located within the mammalian signal sequence of the polypeptide of the interest. Unless the mammalian signal sequence naturally has an intron, a first intron is constructed using any recombinant DNA method known in the art. The first intron comprises a bacterial promoter and signal sequence which overlaps the splice acceptor site. The bacterial promoter and signal sequence are constructed so that they are "operably linked" to the polypeptide sequence, e.g., the IgG heavy chain sequence or light chain sequence. That is, the bacterial promoter is positioned so as to direct transcription of the Fab fragment or scFv sequence in a bacterial cell, and the bacterial signal sequence is positioned to overlap the splice acceptor site so as to result in secretion of the polypeptide into the periplasmic space in a bacterial cell.

To maintain the functionality of the bacterial promoter, the bacterial signal sequence and the mammalian signal and splice acceptor site, the first intron nucleotide sequence may be designed using promoter consensus sequences, signal sequence consensus sequences and splice site consensus sequences which are well known in the art, and as illustrated in the example presented in Section 6. For example, any signal sequence which targets the polypeptide of interest, e.g., an antibody such as IgG, to the bacterial periplasmic membrane, may be used. The bacterial signal sequence may be natural or synthetic in origin. Leader sequences, associated with proteins naturally destined for the periplasm, are, for example, known to direct the secretion of foreign proteins to the periplasm (MacIntyre et al., 1990, Mol. Gen. Genet. 221:466–474). In a preferred embodiment, the signal sequence encodes the pelB sequence and the OmpA protein leader sequence (Hobom et al., 1995, Dev. Biol. Stand. 84:255–262). Other signal sequences are also possible, including, but not limited to, the leaders from $E.$ $coli$ PhoA (Oka et al., 1985, Proc. Natl. Acad. Sci. 82:7212–16), OmpT (Johnson et al., 1996, Protein Expression 7:104–113), LamB and OmpF (Hoffman & Wright, 1985, Proc. Natl. Acad. Sci. USA 82:5107–5111), β-lactamase (Kadonaga et al., 1984, J. Biol. Chem. 259:2149–54), enterotoxins (Morioka-Fujimoto et al., 1991, J. Biol. Chem. 266:1728–32), protein A from $Staphylococcus$ $aureus$ (Abrahmsen et al., 1986, Nucleic Acids Res. 14:7487–7500), endoglucanase from $B.$ $subtilis$ (Lo et al., Appl. Environ. Microbiol. 54:2287–2292), as well as artificial and synthetic signal sequences (MacIntyre et al., 1990, Mol. Gen. Genet. 221:466–74; Kaiser et al., 1987, Science, 235:312–317).

Secretion of Fab fragments or scFv into the periplasm of bacteria may be improved by altering vector sequences, once an initial vector is made. For example, phage display of a single chain fv (scFv) with variability introduced in the signal sequence may be used to select for variants with improved secretion. In addition, other signal peptide coding sequences may also be modified and tried. In this case, a database of signal peptide coding sequences can be made and compare to the desired splice site. The most homologous segment may then be modified if necessary for secretion of Fab in $E.$ $coli$ and retention of Mab expression and secretion in HEK 293 cells.

Individual sequence elements within this region may be optimized by making appropriate changes to improve the functionality of the individual elements, providing the functionality of all sequence elements, i.e., transcription in both bacterial and mammalian hosts, splicing of transcripts in mammalian hosts, and secretion into the periplasm in bacteria and secretion in mammalian hosts, is maintained.

To predict whether modified prokaryotic signal peptides would still retain favorable splice cleavage sites, sequences may be analyzed by SignalP program which uses neural network algorithm (Nielsen et al., 1997, Int. J. Neural Sys. 8, 581 599). The potential functionality of the splice sites may be assessed using the Splice Site Prediction program at the Berkeley Drosophila Genome Project web site (see Reese et al., J. Comput. Biol., 1997, 4(3):311 23). This program also uses a neural network algorithm trained on human genes.

It may also be desirable to add epitope/affinity tags to improve purification or identification of the polypeptide, e.g., Fab fragment, scFv, or light or heavy chain, during purification or screening protocols. In order to insure that these tags be exposed on the protein after secretion, flexible linker sequences such as GGGGS are introduced between the functional domains and the epitope/affinity tag sequences. Peptide tags can include those for which methods/reagents exist that allow facile identification of the tagged polypeptide or fragment, but are unlikely to inhibit or interfere with function of the tagged polypeptide or fragment. The tag may be of any length that permits binding to the corresponding binding reagent, but does not interfere with the tagged proteins binding to the mRNA. In a preferred embodiment, the tag is about 8, 10, 12, 15, 18 or 20 amino acids, is less than 15, 20, 25, 30, 40 or 50 amino acids, but may be 100, 150, 200, 300, 400 or 500 or more amino acids in length. The tag may be bound specifically by a reagent that does not bind any component of: (1) the cell of interest; or (2) a polysomal preparation of interest; or (3) whatever cellular fraction of interest is being contacted by the reagent that binds the tag. Molecular tags may include, by way of example, and not by limitation, protein A fragments; myc epitopes (Evan et al., Mol. Cell Biol. 5(12): 3610–3616); Btag (Wang et al., 1996, Gene 169(1):53–58; and polyhistidine tracts (Bornhorst et al., 2000, Methods Enzymol 326:245–54). Other preferred tags include, but are not limited to:

(1) a portion of the influenza virus hemagglutinin protein (Tyr-Pro-Tyr-Asp-Val-Pro-Asp-Tyr-Ala; SEQ ID NO: 1). The reagent used for purification is a monoclonal antibody recognizing the tagged protein (12CA5) (Wilson et al., 1984, Cell 37(3):767 78).

(2) a portion of the human c myc gene (Glu-Gln-Lys-Leu-Ile-Ser-Glu-Glu-Asp-Leu; SEQ ID NO: 2). The reagent used for purification is a monoclonal antibody recognizing the tagged protein (9E10) (Evan et al., 1985, Mol Cell Biol. 5(12):3610 6).

(3) a portion of the bluetongue virus VP7 protein (Gln-Tyr-Pro-Ala-Leu-Thr; SEQ ID NO:3). The reagent used for purification is a monoclonal antibody recognizing the tagged protein (D11 and/or F10) (Wang et al., Gene. 1996 Feb. 22;169(1):53 8)

(4) a FLAG peptide (e.g., Asp-Tyr-Lys-Asp-Asp-Asp-Asp-Lys; SEQ ID NO: 4). The reagent used for purification are monoclonal antibodies recognizing the tagged protein (e.g., M1 and/or M2) (Sigma) (Hopp et al., U.S. Pat. No. 4,703,004, entitled "Synthesis of protein with an identification peptide" issued Oct. 27, 1987; Brizzard et al., 1994, Biotechniques. April;16(4):730 5; Knappik et al., 1994, Biotechniques 17(4):754 761);

(5) a Strep tag peptide (e.g., Ala Trp Arg His Pro Gln Phe Gly Gly; SEQ ID NO: 5). In a preferred embodiment, a strep-tag peptide is used. The reagent used for purification is one of several optimized versions of streptavidin that recognizes the tagged protein (IBA GmbH) (Skerra et al., U.S. Pat. No. 5,506,121, entitled Fusion peptides with binding activity for streptavidin, issued Apr. 9, 1996; Skerra et al., 1999, Biomol. Eng. 16(1 4):79 86; Skerra et al., 2000, Methods Enzymol. 2000;326:271 304).

When the soluble domain/fragment of the polypeptide that is to be expressed in bacteria is not co-terminal with the full-length polypeptide of interest, a second intron comprising a bacterial stop codon is included in the polypeptide of the interest. This intron is located in the region of the polypeptide where termination of the soluble domain/fragment is desired. If an intron does not naturally exist in the desired location of the protein of interest, appropriate intron sequences may be introduced into the desired location using recombinant or synthetic DNA techniques well known in the art. For example, in a preferred embodiment, the sequence of the heavy chain of IgG comprises a second intron located between the CH1 domain and the hinge region. Translation termination at this site in bacteria results in the expression of a $Fab_1$ fragment. Alternatively, if production of a $Fab_2$ fragment is desired, an intron comprising a stop codon may be included in the sequence encoding the polypeptide between the hinge and the CH2 domain. This would result in the production of the larger $Fab_2$ fragment.

Dual expression vector cassette sequences are tested to insure that the functionality of the splice site acceptor and bacterial signal sequences are maintained. Any sequence changes which negatively impact the ability of the full-length IgG to be secreted from mammalian cells would be not be useful, although minor functional consequences could be tolerated, at least for screening purposes.

Circular vectors incorporating IgG and Fab expression sequences may be constructed using standard methods known in the art (see Sambrook et al., 1989*, supra*; Ausubel et al., Current Protocols in Molecular Biology, Greene Publishing Associates and Wiley Interscience, New York). For example, synthetic or recombinant DNA technology may be used. In one embodiment, a vector comprising The dual expression vector cassette sequences is made by polymerase chain reaction ("PCR") amplification. In this method, oligonucleotides are synthesized to include restriction enzyme sites at their 5' ends, and PCR primer sequences complementary to the boundary sequences of an IgG regulatory and coding sequence at their 3' ends. These oligonucleotides are then used as primers in a PCR amplification reaction to amplify the IgG regulatory and coding sequence region. This amplified region is then cloned into a vector containing mammalian and bacterial origins of replication and appropriate selectable marker sequences, using standard molecular biology techniques (see e.g., Methods in Enzymology, 1987, Volume 154, Academic Press; Sambrook et al., 1989, *supra*; and Ausubel et al., *supra*). The circular product is then transformed into *Escherichia coli* for amplification to yield large amounts of the vector.

Preferably, as discussed in detail below, the vector includes a bacterial origin of replication, a mammalian origin of replication, and one or more selectable markers. As the dual expression vector system described herein is designed to be used in both mammalian and bacterial hosts, a variety of bacterial strains or cell line may be used. The choice of certain vector sequences, such as the origin of replication sequences, will depend on the choice of host, which, in turn may depend on a variety of factors, such as factors required for expression, secretion, and screening or selecting a particular polypeptide or antibody of interest.

5.1.2 Methods for Production of Antibodies

Antibodies which immunospecifically bind to an antigen can be produced by any method known in the art for the synthesis of antibodies, in particular, by chemical synthesis or preferably, by recombinant expression techniques.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T Cell Hybridomas 563 681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a non-murine antigen and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody wherein, preferably, the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments which recognize specific particular epitopes may be generated by any technique known to those of skill in the art. For example, Fab and F(ab')2 fragments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of interest. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65 93). For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules such as antibodies having a variable region derived from a human antibody and a non-human immunoglobulin constant region. Methods for producing chimeric antibodies are known in the art. See e.g., Morrison, 1985, Science 229:1202; Oi et al., 1986, BioTechniques 4:214; Gillies et al., 1989, J. Immunol. Methods 125: 191–202; and U.S. Pat. Nos. 5,807,715, 4,816,567, and 4,816,397, which are incorporated herein by reference in their entirety. Chimeric antibodies comprising one or more CDRs from human species and framework regions from a non-human immunoglobulin molecule can be produced using a variety of techniques known in the art including, for example, CDR-grafting (EP 239,400; PCT publication No. WO 91/09967; and U.S. Pat. Nos. 5,225,539, 5,530,101, and 5,585,089), veneering or resurfacing (EP 592,106; EP 519, 596; Padlan, 1991, Molecular Immunology 28(4/5): 489–498; Studnicka et al., 1994, Protein Engineering 7(6): 805–814; and Roguska et al., 1994, PNAS 91:969–973), and chain shuffling (U.S. Pat. No. 5,565,332). In a preferred embodiment, chimeric antibodies comprise a human CDR3 having an amino acid sequence of any one of the CDR3 listed in Table 2 and non-human framework regions. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Further, the antibodies of interest can, in turn, be utilized to generate anti-idiotype antibodies that "mimic" antigens using techniques well known to those skilled in the art. (See, e.g., Greenspan & Bona, 1989, FASEB J. 7(5):437–444; and Nissinoff, 1991, J. Immunol. 147(8):2429–2438). For example, antibodies that bind to and competitively inhibit the binding of an antigen of interest (as determined by assays well known in the art and disclosed in *supra*) to its host cell receptor can be used to generate anti-idiotypes that "mimic" an antigen of interest binding domain and, as a consequence, bind to and neutralize the antigen and/or its host cell receptor. Such neutralizing anti-idiotypes or Fab fragments of such anti-idiotypes can be used in therapeutic regimens to neutralize the antigen. For example, such anti-idiotypic antibodies can be used to bind an antigen of interest and/or to bind its host cell receptor.

5.1.3 Recombinant Expression and Protein Production

Once the dual expression vector containing a cassette sequence encoding a polypeptide of interest is constructed, e.g., a cassette sequence encoding an antibody molecule with the appropriately designed intron sequences, the dual expression vector of the invention may be produced by recombinant DNA technology using techniques well-known in the art. See, e.g., U.S. Pat. No. 6,331,415, which is incorporated herein by reference in its entirety.

For example, in a preferred embodiment, methods which are well known to those skilled in the art can be used to construct the dual expression vector cassette with appropriate transcriptional and translational control signals. These methods include, for example, in vitro recombinant DNA techniques, synthetic techniques, and in vivo genetic recombination. The invention, thus, provides an expression vector comprising a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy, the entire light chain, or both the entire heavy and light chains.

The dual expression vector is transferred to a host cell by conventional techniques and the transfected cells are then cultured by conventional techniques to produce an antibody of interest. Thus, the invention includes host cells containing a polynucleotide encoding an antibody of interest or fragments thereof, or a heavy or light chain thereof, or portion thereof, or a single chain antibody of interest, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host systems may be utilized to express the dual expression vector of the invention (see, e.g., U.S. Pat. No. 5,807,715). Such host systems represent cells which may, when transformed or transfected with the appropriate nucleotide coding sequences, express an antibody molecule of interest in situ. These include but are not limited to microorganisms such as bacteria (e.g., *E. coli* and *B. subtilis*); yeast (e.g., Saccharomyces Pichia) transformed with dual expression vectors; insect cell systems infected with recombinant virus expression vectors (e.g., baculovirus); plant cell systems infected with recombinant virus expression vectors (e.g., cauliflower mosaic virus, CaMV; tobacco mosaic virus, TMV) transformed with dual expression cassettes; or mammalian cell systems (e.g., COS, HEK, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

For expression in a bacterial host, the dual expression vector includes an origin of replication, which is needed for replication and propagation of the plasmid vector. For cloning and propagation in *E. coli*, any *E. coli* origin of replication is used, examples of which are well-known in the art (see, Miller, 1992, A Short Course in Bacterial Genetics, Cold Spring Harbor Laboratory Press, NY, and references therein). Non-limiting examples of readily available plasmid origins of replication are ColE1-derived origins of replication (Bolivar et al., 1977, Gene 2:95–113; see Sambrook et al., 1989, *supra*), p15A origins present on plasmids such as pACYC184 (Chang and Cohen, 1978, J. Bacteriol. 134: 1141–56; see also Miller, 1992, p. 10.4–10.11), and pSC101 origin available for low-copy plasmids expression are all well known in the art.

For example, in one embodiment, the origin of replication from a high-copy plasmid is used, such as a plasmid containing a ColE1-derived origin of replication, examples of which are well known in the art (see Sambrook et al., 1989, *supra*; see also Miller, 1992, A Short Course in Bacterial Genetics, Cold Spring Harbor Laboratory Press, NY, and references therein). One example is an origin from pUC19 and its derivatives (Yanisch-Perron et al., 1985, Gene 33:103–119). pUC vectors exist at levels of 300–500 copies per cell and have convenient cloning sites for insertion of foreign genes. For very high expression, λ vectors, such as λgt11 (Huynh et al., 1984, in "DNA Cloning Techniques:, Vol I: A Practical Approach", D. Glover, ed., pp 49–78, IRL Press, Oxford), or the T7 or SP6 phage promoters in cells containing T7 and Sp6 polymerase expression systems (Studier et al., 1990, Methods Enzymol. 185:60–89) can be used.

When a lower level of expression is desired, an origin of replication from a medium or a low-copy may be used. Medium-copy plasmids are well known in the art, such as pBR322, which has a ColE1 derived origin of replication and 20–100 copies per cell (Bolivar et al, 1977, Gene 2:95–113; see Sambrook et al., 1989, *supra*), or pACYC184, one of the pACYC100 series of plasmids, which have a p15A origin of replication and exist at 10–12 copies per cell (Chang and Cohen, 1978, J. Bacteriol. 134:1141–56; see also Miller, 1992, p. 10.4–10.11). Low-copy plasmids are also well known in the art, for example, pSC101, which has a pSC101 origin, and approximately 5 copies per cell. Both pACYC and pSC101 plasmid vectors have convenient cloning sites and can co-exist in the same cell as pBR and pUC plasmids, since they have compatible origins of replication and unique selective antibiotic markers. Other suitable plasmid origins of replication include lambda or phage P1 replicon based plasmids, for example the Lorist series (Gibson et al., 1987, Gene 53: 283–286).

When even less expression is desired, the origin of replication may be obtained from the bacterial chromosome (see Miller, 1992, *supra*; Niedhardt, F. C., ed., 1987, *Escherichia coli* and *Salmonella typhimurium*, American Society for Microbiology, Washington, D.C.; Yarmolinsky, M. B. & Sternberg, N., 1988, pp. 291–438, in Vol. 1 of *The Bacteriophages*, R. Calendar, ed., Plenum Press, New York). In addition, synthetic origins of replication, bacterial promoters, or bacterial signal sequences may be used.

In mammalian host cells, the dual expression vector sequences may either be designed to exist in the mammalian host cells as episomes, or may be designed to facilitate integration into the host genomic DNA to create stable cell lines, e.g., by designing vector to be linearized. Such vectors are known in the art.

For example, a number of viral-based expression systems may be utilized in mammalian host cells. In cases where an adenovirus is used as an expression vector, The dual expression vector cassette sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing IgG gene products in infected hosts (e.g., see Logan and Shenk, 1984, Proc. Natl. Acad. Sci. USA 81, 3655–3659). Specific initiation signals may also be required for efficient translation of inserted expression vector cassette sequences. These signals include the ATG initiation codon and adjacent sequences. In cases where an IgG heavy or light chain, including its own initiation codon and adjacent sequences, is inserted into the appropriate expression vector, no additional translational control signals may be needed. However, in cases where only a portion of the IgG coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153, 516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI 38, BT483, Hs578T, HTB2, BT20 and T47D, NS0 (a murine myeloma cell line that does not endogenously produce any immunoglobulin chains).

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8–17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62: 191–217; May, 1993, TIB TECH 11(5):155–215); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., 1981, J. Mol. Biol. 150:1, which are incorporated by reference herein in their entireties.

For selection in bacteria, preferably antibiotic resistance markers are used, such as the kanamycin resistance gene from Tn903 (Friedrich and Soriano, 1991, Genes Dev. 5:1513–1523), or genes that confer resistance to other aminoglycosides (including but not limited to dihydrostreptomycin, gentamycin, neomycin, paromycin and streptomycin), the TEM-1 β-lactamase gene from Tn9, which confers resistance to penicillin (including but not limited to ampicillin, carbenicillin, methicillin, penicillin N, penicillin O and penicillin V). Other selectable genes sequences including, but not limited to gene sequences encoding polypeptides which confer zeocin resistance (Hegedus et al. 1998,

*Gene* 207:241–249). Other antibiotics that can be utilized are genes that confer resistance to amphenicols, such as chloramphenicol, for example, the coding sequence for chloramphenicol transacetylase (CAT) can be utilized (Eikmanns et al. 1991, Gene 102:93–98). As will be appreciated by one skilled in the art, other non-antibiotic methods to select for maintenance of the plasmid may also be used, such as, for example a variety of auxotrophic markers (see Sambrook et al., 1989, *supra*; Ausubel et al., *supra*).

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two dual expression vectors of the invention, the first vector encoding a heavy chain derived polypeptide and the second vector encoding a light chain derived polypeptide. The two vectors may contain identical selectable markers which enable equal expression of heavy and light chain polypeptides in mammalian cells and Fab or scFv polypeptides in bacterial cells. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2 197). The coding sequences for the heavy and light chains may comprise cDNA or genomic DNA.

Polypeptides can be produced by standard recombinant DNA techniques. For example, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al., eds., John Wiley & Sons, 1992). Moreover, a nucleic acid encoding a bioactive molecule can be cloned into an expression vector containing the Fc domain or a fragment thereof such that the bioactive molecule is linked in-frame to the Fc domain or Fc domain fragment.

Methods for fusing or conjugating polypeptides to the constant regions of antibodies are known in the art. See, e.g., U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; PCT publications WO 91/06570, WO 96/04388, WO 96/22024, WO 97/34631, and WO 99/04813; Ashkenazi et al., 1991, Proc. Natl. Acad. Sci. USA 88: 10535 10539; Traunecker et al., 1988, Nature, 331:84 86; Zheng et al., 1995, J. Immunol. 154:5590 5600; and Vil et al., 1992, Proc. Natl. Acad. Sci. USA 89:11337 11341, which are incorporated herein by reference in their entireties.

The nucleotide sequences encoding a bioactive molecule and an Fc domain or fragment thereof may be an be obtained from any information available to those of skill in the art (i.e., from Genbank, the literature, or by routine cloning). The nucleotide sequence coding for a polypeptide a fusion protein can be inserted into the dual expression vector.

The expression of the polypeptide in eukaryotic cells may be controlled by any promoter or enhancer element known in the art. Promoters which may be used to control the expression of the gene encoding fusion protein include, but are not limited to, the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), the tetracycline (Tet) promoter (Gossen et al., 1995, Proc. Nat. Acad. Sci. USA 89:5547 5551); and in bacteria, prokaryotic promoters such as the β-lactamase promoter (Villa-Kamaroff et al., 1978, Proc. Natl. Acad. Sci. U.S.A. 75:3727–3731), or the tac promoter (DeBoer et al., 1983, Proc. Natl. Acad. Sci. U.S.A. 80:21–25; see also "Useful proteins from recombinant bacteria" in Scientific American, 1980, 242:74–94); in plant cells, the nopaline synthetase promoter region (Herrera-Estrella et al., Nature 303:209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, and the alkaline phosphatase promoter.

In a specific embodiment, the expression of a polypeptide is regulated by a constitutive promoter, such as the CMV promoter. In another embodiment, the expression of a polypeptide is regulated by an inducible promoter.

Expression vectors containing inserts of a gene encoding a polypeptide can be identified by three general approaches: (a) nucleic acid hybridization, (b) presence or absence of "marker" gene functions, and (c) expression of inserted sequences. In the first approach, the presence of a gene encoding a polypeptide in an expression vector can be detected by nucleic acid hybridization using probes comprising sequences that are homologous to an inserted gene encoding the polypeptide, respectively. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a polypeptide in the vector. For example, if the nucleotide sequence encoding the fusion protein is inserted within the marker gene sequence of the vector, recombinants containing the gene encoding the fusion protein insert can be identified by the absence of the marker gene function. In the third approach, recombinant expression vectors can be identified by assaying the gene product (e.g., fusion protein) expressed by the recombinant. Such assays can be based, for example, on the physical or functional properties of the fusion protein in in vitro assay systems, e.g., binding with anti bioactive molecule antibody.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of IgG heavy or light chain in mammalian cells may be regulated by a second nucleic acid sequence so that the IgG heavy or light chain is expressed in a host transformed with the recombinant DNA molecule. For example, expression of IgG heavy or light chain may be controlled by any promoter/enhancer element known in the art.

Preferably, the bacterial expression of Fab fragments or full-length IgG is controlled by an inducible promoter. Inducible expression yielding a wide range of expression can be obtained by utilizing a variety of inducible regulatory sequences. In one embodiment, for example, the lacI gene and its gratuitous inducer IPTG can be utilized to yield inducible, high levels of expression of Fab fragments in *E. coli* when sequences encoding such polypeptides are transcribed via the lacOP regulatory sequences. A variety of other inducible promoter systems are well known to those of skill in the art which can also be utilized. Levels of expression from IgG dual expression vector system can also be varied by using promoters of different strengths.

Other regulated expression systems that can be utilized include but are not limited to, the araC promoter which is inducible by arabinose (AraC) (see, e.g., Schleif, 2000, Trends Genet. 16:559–565), the TET system (Geissendorfer and Hillen, 1990, Appl. Microbiol. Biotechnol. 33:657–663), the pL promoter of phage λ temperature and the inducible lambda repressor C1857 (Pirrotta, 1975, Nature 254: 114–117; Petrenko et al., 1989, Gene 78:85–91), the trp promoter and trp repressor system (Bennett et al., 1976, Proc. Natl. Acad. Sci USA 73:2351–55; Wame et al., 1986, Gene 46:103–112), the lacUV5 promoter (Gilbert and Maxam, 1973, Proc. Natl. Acad. Sci. USA 70:1559–63), 1pp (Nokamura et al., 1982, J. Mol. Appl. Gen. 1:289–299), the T7 gene-10 promoter, phoA (alkaline phosphatase), recA (Horii et al., 1980, Proc. Natl. Acad. Sci. USA 77:313 7), and the tac promoter, a trp-lac fusion promoter, which is inducible by IPTG (Amann et al., 1983, Gene 25:167–78), for example, are all commonly used strong promoters, resulting in an accumulated level of about 1 to 10% of total cellular protein for a protein whose level is controlled by each promoter. If a stronger promoter is desired, the tac promoter is approximately tenfold stronger than lacUV5, but will result in high baseline levels of expression, and should be used only when overexpression is required. If a weaker promoter is required, other bacterial promoters are well known in the art, for example, maltose, galactose, or other desirable promoter (sequences of such promoters are available from GenBank (Burks et al. 1991, Nucl. Acids Res. 19:2227–2230).

For eukaryotic expression of full-length IgG heavy or light chain, vectors will include eukaryotic-specific replication origins and promoter regions, which include specific sequences that are sufficient for RNA polymerase recognition, binding and transcription initiation. Additionally, promoter regions include sequences that modulate the recognition, binding and transcription initiation activity of RNA polymerase. Such sequences may be cis acting or may be responsive to trans acting factors. Depending upon the nature of the regulation, promoters may be constitutive or regulated. Promoters that may be used to control TnpI expression include, but are not limited to, the SV40 early promoter region (Benoist and Chambon, 1981, Nature 290: 304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci; U.S.A. 78:1441–1445), the regulatory sequences of the metallothionein gene (Brinster et al., 1982, Nature 296:39–42); plant expression vectors comprising the nopaline synthetase promoter region (Herrera-Estrella et al., 1984, Nature 303: 209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, or the ADC (alcohol dehydrogenase) promoter.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the cloned DNA to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression (see, e.g., Kozak, 1991, J. Biol. Chem. 266:19867). Similarly, alternative codons, encoding the same amino acid, can be substituted for coding sequences in order to enhance translation (e.g., the codon preference of the host cell can be adopted, the presence of G-C rich domains can be reduced, and the like).

The vector may also contain nucleotide sequences of interest for protein expression, manipulation or maintenance of the inserted target DNA. For example, promoter sequences, enhancer sequences, translation sequences such as Shine and Dalgarno sequences, transcription factor recognition sites, Kozak consensus sequences, and termination signals may be included, in the appropriate position in the vector.

The vector should also include signal sequences which may be natural or synthetic in origin. Signal sequences which may target polypeptides, e.g., antibodies such as IgG, to the inner cell membrane can also be used. Leader sequences, associated with proteins naturally destined for the periplasm, are, for example, known to direct the secretion of foreign proteins to the periplasm (MacIntyre et al., 1990, Mol. Gen. Genet. 221:466–474). In a preferred embodiment, the signal sequence encodes the OmpA protein leader sequence (Hobom et al., 1995, Dev. Biol. Stand. 84:255–262). Other signal sequences are also possible, including, but not limited to, the leaders from *E. coli* PhoA (Oka et al., 1985, Proc. Natl. Acad. Sci 82:7212–16), OmpT (Johnson et al., 1996, Protein Expression 7:104–113), LamB and OmpF (Hoffman & Wright, 1985, Proc. Natl. Acad. Sci. USA 82:5107–5111), β-lactamase (Kadonaga et al., 1984, J. Biol. Chem. 259:2149–54), enterotoxins (Morioka-Fujimoto et al., 1991, J. Biol. Chem. 266:1728–32), protein A from *Staphylococcus aureus* (Abrahmsen et al., 1986, Nucleic Acids Res. 14:7487–7500), endoglucanase from *B. subtilis* (Lo et al., Appl. Environ. Microbiol. 54:2287–2292), as well as artificial and synthetic signal sequences (MacIntyre et al., 1990, Mol. Gen. Genet. 221:466–74; Kaiser et al., 1987, Science, 235:312–317).

Any method known in the art for delivering a DNA preparation comprising the dual expression vector cassette sequences into a host cell is suitable for use with the methods described above. Such methods are known in the art and include, but are not limited to electroporation of cells, preparing competent cells with calcium or rubidium chloride, and transduction of DNA with target DNA packaged in viral particles. For eukaryotic cells, methods include but are not limited to electroporation, transfection with calcium phosphate precipitation of DNA, and viral packaging. In a preferred embodiment, electroporation is used. Cells are treated to make them competent for electroporation by standard methods (see Ausubel et al., Current Protocols in Molecular Biology, Greene Publishing Associates and Wiley Interscience, New York). Preferably, about 50 µl of a standard preparation of electrocompetent cells is used for electroporation by standard procedures. In experiments that require the transformation of a linear or circular vector, 0.3 µg or more of vector is preferably used. In experiments that require the transformation of a DNA preparation containing the IgG DNA, 0.3 µg or more is preferably used. For co-transformation experiments, the DNAs are preferably mixed before electroporation. After electroporation, the cells are preferably diluted in culture medium and incubated for an approximately 1 and a half hours recovery period before culturing under conditions to identify the phenotypic change conveyed by the selectable marker gene.

Optimally, the phenotypic change is resistance to an antibiotic and the cells are cultured on plates that contain the corresponding antibiotic. In this case, the antibiotic resistant colonies that appear after overnight culture will predominantly contain the desired subcloning product. For the selectable marker, preferably antibiotic resistance markers are used, such as the kanamycin resistance gene from Tn903 (Friedrich and Soriano, 1991, Genes Dev. 5:1513–1523), or genes that confer resistance to other aminoglycosides (including but not limited to dihydrostreptomycin, gentamycin, neomycin, paromycin and streptomycin), the TEM-1 β-lactamase gene from Tn9, which confers resistance to penicillin (including but not limited to ampicillin, carbenicillin, methicillin, penicillin N, penicillin O and penicillin V). Other selectable genes sequences including, but not limited to gene sequences encoding polypeptides which confer zeocin resistance (Hegedus et al. 1998, Gene 207:241–249). Other antibiotics that can be utilized are genes that confer resistance to amphenicols, such as chloramphenicol, for example, the coding sequence for chloramphenicol transacetylase (CAT) can be utilized (Eikmanns et al. 1991, Gene 102:93–98). As will be appreciated by one skilled in the art, other non-antibiotic methods to select for maintenance of the plasmid may also be used, such as, for example a variety of auxotrophic markers (see Sambrook et al., 1989, supra; Ausubel et al., supra).

In another embodiment, DNA is delivered into the host cell by transduction of DNA that has been packaged into a phage particle. P1 or λ transduction and packaging protocols are known in the art. Lambda packaging extracts are available commercially (e.g., from Promega, Madison, Wis.).

Once an antibody molecule of interest has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

5.2 Methods for Selecting and Screening Antibodies 5.2.1 Methods for Selection and Characterization of Antibodies Full-length IgG and Fab fragments of the present invention may be characterized in a variety of ways. In particular, full-length IgG and Fab fragments may be assayed for the ability to immunospecifically bind to an antigen of interest. Such an assay may be performed in solution (e.g., Houghten, 1992, Bio/Techniques 13:412 421), or on a solid support such as a microtiter dish, or on beads (Lam, 1991, Nature 354:82 84), on chips (Fodor, 1993, Nature 364:555 556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865 1869) or on phage (Scott and Smith, 1990, Science 249:386 390; Devlin, 1990, Science 249:404 406; Cwirla et al., 1990, Proc. Natl. Acad. Sci. USA 87:6378 6382; and Felici, 1991, J. Mol. Biol. 222:301 310) (each of these references is incorporated herein in its entirety by reference). Antibodies or fragments thereof that have been identified to immunospecifically bind to an antigen of interest or a fragment thereof can then be assayed for their specificity and affinity for an antigen of interest.

The antibodies of interest or fragments thereof may be assayed for immunospecific binding to an antigen of interest and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of the present invention or a fragment thereof for an antigen of interest and the binding off-rates can be determined from the data by scatchard plot analysis. Competition with a second antibody can also be determined using radioimmunoassays. In this case, an antigen of interest is incubated with an antibody of the present invention or a fragment thereof conjugated to a labeled compound (e.g., $^3$H or $^{125}$I) in the presence of increasing amounts of an unlabeled second antibody.

In a preferred embodiment, BIAcore kinetic analysis is used to determine the binding on and off rates of antibodies or fragments thereof to an antigen of interest. BIAcore kinetic analysis comprises analyzing the binding and dissociation of an antigen of interest from chips with immobilized antibodies or fragments thereof on their surface (see the Example section infra).

Antibodies or fragments thereof can also be assayed for their ability to inhibit the binding of an antigen of interest to its host cell receptor using techniques known to those of skill in the art. For example, cells expressing the receptor for an antigen of interest can be contacted with the antigen in the presence or absence of the antibody or fragment thereof, i.e., the Fab fragment, and the ability of the antibody or fragment thereof to inhibit an antigen of interest's binding can be measured by, for example, flow cytometry or a scintillation assay. The antigen of interest or the antibody or antibody fragment can be labeled with a detectable compound such as a radioactive label (e.g., 32P, 35S, and 125I) or a fluorescent label (e.g., fluorescein isothiocyanate, rhodamine, phycoerythrin, phycocyanin, allophycocyanin, o-phthaldehyde and fluorescamine) to enable detection of an interaction between an antigen of interest and its host cell receptor. Alternatively, the ability of antibodies or fragments thereof to inhibit an antigen of interest from binding to its receptor can be determined in cell-free assays. For example, the antigen of interest can be contacted with an antibody or Fab fragment and the ability of the antibody or antibody fragment to inhibit an antigen of interest from binding to its host cell receptor can be determined. Preferably, the antibody or Fab fragment is immobilized on a solid support and the antigen of interest is labeled with a detectable compound. Alternatively, the antigen of interest is immobilized on a solid support and the antibody or Fab fragment is labeled with a detectable compound. The antigen of interest may be partially or completely purified (e.g., partially or completely free of other polypeptides) or part of a cell lysate. Further, an antigen may be a fusion protein comprising the antigen and a domain, such as a binding domain. Alternatively, an antigen can be biotinylated using techniques well known to those of skill in the art (e.g., biotinylation kit, Pierce Chemicals; Rockford, Ill.).

The antibodies of interest or fragments thereof can also be assayed for their ability to inhibit or downregulate an activity of the antigen, using techniques known to those of skill in the art. The antibodies or Fab fragments produced by the vector system of the invention can also be assayed for their ability to inhibit or downregulate the expression of an antigenic polypeptide. Techniques known to those of skill in the art, including, but not limited to, Western blot analysis, Northern blot analysis, and RT-PCR can be used to measure protein expression.

The antibodies or Fab fragments produced by the vector system of the invention are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a subject tissue sample is grown in culture, and exposed to or otherwise administered an antibody or composition of the present invention, and the effect of such an antibody or composition of the present invention upon the tissue sample is observed. In various specific embodiments, in vitro assays can be carried out to determine if an antibody or composition of the present invention has a desired effect upon specific cell types. Preferably, the antibodies or Fab fragments produced by the vector system of the invention are also tested in in vitro assays and animal model systems prior to administration to humans. Further, in accordance with this embodiment, the tissues from the sacrificed rats can be examined for histological changes.

In accordance with the invention, clinical trials with human subjects need not be performed in order to demonstrate the prophylactic and/or therapeutic efficacy of antibodies or Fab fragments produced by the vector system of the invention. In vitro and animal model studies using the antibodies or fragments thereof can be extrapolated to humans and are sufficient for demonstrating the prophylactic and/or therapeutic utility of said antibodies or antibody fragments.

Antibodies or compositions of the present invention for use in therapy can be tested for their toxicity in suitable animal model systems, including but not limited to rats, mice, cows, monkeys, and rabbits. For in vivo testing of an antibody or composition's toxicity any animal model system known in the art may be used.

Efficacy in treating or preventing viral infection may be demonstrated by detecting the ability of antibodies or Fab fragments produced by the vector system of the invention to inhibit infection of a pathogen, or to prevent, ameliorate or alleviate one or more symptoms associated with the antigen. The treatment is considered therapeutic if there is, for example, amelioration of one or more symptoms, or a decrease in mortality and/or morbidity following administration of an antibody or composition of interest. Further, the treatment is considered therapeutic if there is an increase in the immune response following the administration of one or more antibodies or Fab fragments produced by the vector system of the invention which immunospecifically bind to one or more antigens.

Antibodies or compositions of interest can be tested in vitro and in vivo for the ability to induce the expression of cytokines such as IFN-α, IFN-β, IFN-γ, IL-2, IL-3, IL-4, IL-5, IL-6, IL-7, IL-8, IL-9, IL-10, IL-12 and IL-15. Techniques known to those of skill in the art can be used to measure the level of expression of cytokines. For example, the level of expression of cytokines can be measured by analyzing the level of RNA of cytokines by, for example, RT-PCR and Northern blot analysis, and by analyzing the level of cytokines by, for example, immunoprecipitation followed by western blot analysis and ELISA. In a preferred embodiment, an antibody or Fab fragment produced by the vector system of the invention is tested for its ability to induce the expression of IFN-γ.

Antibodies or compositions of interest can be tested in vitro and in vivo for their ability to modulate the biological activity of immune cells, preferably human immune cells (e.g., T-cells, B-cells, and Natural Killer cells). The ability of an antibody or Fab fragment produced by the vector system of interest to modulate the biological activity of immune cells can be assessed by detecting the expression of antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by 3H thymidine incorporation assays and trypan blue cell counts. Antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs).

Antibodies or compositions of interest can also be tested for their ability to inhibit viral replication or reduce viral load in in vitro, ex vivo and in vivo assays. Antibodies or Fab fragments produced by the vector system of the invention can also be tested for their ability to decrease the time course of an infection. antibodies or Fab fragments produced by the vector system of the invention can also be tested for their ability to increase the survival period of humans suffering from infection by at least 25%, preferably at least 50%, at least 60%, at least 75%, at least 85%, at least 95%, or at least 99%. Further, antibodies or Fab fragments produced by the vector system of the invention can be tested for their ability reduce the hospitalization period of humans suffering from infection by at least 60%, preferably at least 75%, at least 85%, at least 95%, or at least 99%. Techniques known to those of skill in the art can be used to analyze the function of the antibodies or compositions of interest in vivo.

5.2.2 Methods of Screening Using Phage Display

As will be apparent to one of ordinary skill in the art, there are numerous other methods of screening individual proteins or other compounds, as well as large libraries of proteins or other compounds (e.g., phage display libraries) to identify molecules which bind to a particular antigen of interest.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest of interest can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41–50; Ames et al., 1995, J. Immunol. Methods 184:177–186; Kettleborough et al., 1994, Eur. J. Immunol. 24:952–958; Persic et al., 1997, Gene 187:9–18; Burton et al., 1994, Advances in Immunology 57:191–280; PCT application No. PCT/GB91/O1 134; PCT publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580, 717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

Examples of phage display libraries are described in Scott and Smith, 1990, Science 249:386–390; Devlin et al., 1990, Science, 249:404–406; Christian et al., 1992, J. Mol. Biol. 227:711–718; Lenstra, 1992, J. Immunol. Meth. 152:149–157; Kay et al., 1993, Gene 128:59 65; and PCT Publication No. WO 94/18318 dated Aug. 18, 1994.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864–869; Sawai et al., 1995, AJRI 34:26–34; and Better et al., 1988, Science 240:1041–1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1α promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

5.2.3 Methods for Optimization of Antibody Sequences

In addition to its above-described applications for testing and characterizing novel antibodies, the dual expression vector may be used for optimization of existing antibodies for desired binding or therapeutic properties. In this aspect of the invention, nucleotide sequences encoding known IgG heavy or light chain sequences may be cloned in the dual expression vector system, and subjected to chemical, synthetic or genetic mutagenesis to alter its nucleotide sequence. Sequence variants may then be screened in bacteria and/or human cells for changes in characteristics of interest.

A polynucleotide encoding an antibody may be obtained, and the nucleotide sequence determined, by any method known in the art. The nucleotide sequence of antibodies immunospecific for a desired antigen can be obtained, e.g., from the literature or a database such as GenBank. Since the amino acid sequences of VITAXIN™ is known, nucleotide sequences encoding this antibody can be determined using methods well known in the art, i.e., nucleotide codons known to encode particular amino acids are assembled in such a way to generate a nucleic acid that encodes the antibody. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of interest) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs is inserted within framework regions using routine recombinant DNA techniques. The framework regions may be naturally occurring or consensus framework regions, and preferably human framework regions (see, e.g., Chothia et al., 1998, J. Mol. Biol. 278: 457–479 for a listing of human framework regions). Preferably, the polynucleotide generated by the combination of the framework regions and CDRs encodes an antibody that specifically binds to a particular antigen. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

Non-limiting examples of commercially available antibodies which may be used in accordance with the present invention are found in Table 1 below.

TABLE 1

Therapeutic Antibodies That Can Be Optimized According to the Methods of the Invention

| Company | Product | Disease | Target |
|---|---|---|---|
| Abgenix | ABX-EGF | Cancer | EGF receptor |
| AltaRex | OvaRex | ovarian cancer | tumor antigen CA 125 |
|  | BravaRex | metastatic cancers | tumor antigen MUC1 |
| Antisoma | Theragyn (pemtumomabytrrium-90) | ovarian cancer | PEM antigen |
|  | Therex | breast cancer | PEM antigen |

TABLE 1-continued

Therapeutic Antibodies That Can Be Optimized
According to the Methods of the Invention

| Company | Product | Disease | Target |
|---|---|---|---|
| Boehringer Ingelheim | blvatuzumab | head & neck cancer | CD44 |
| Centocor/J&J | Panorex | Colorectal cancer | 17-1A |
| | ReoPro | PTCA | gp IIIb/IIIa |
| | ReoPro | Acute MI | gp IIIb/IIIa |
| | ReoPro | Ischemic stroke | gp IIIb/IIIa |
| Corixa | Bexocar | NHL | CD20 |
| CRC Technology | MAb, idiotypic 105AD7 | colorectal cancer vaccine | gp72 |
| Crucell | Anti-EpCAM | cancer | Ep-CAM |
| Cytoclonal | MAb, lung cancer | non-small cell lung cancer | NA |
| Genentech | Herceptin | metastatic breast cancer | HER-2 |
| | Herceptin | early stage breast cancer | HER-2 |
| | Rituxan | Relapsed/refractory low-grade or follicular NHL | CD20 |
| | Rituxan | intermediate & high-grade NHL | CD20 |
| | MAb-VEGF | NSCLC, metastatic | VEGF |
| | MAb-VEGF | Colorectal cancer, metastatic | VEGF |
| | AMD Fab | age-related macular degeneration | CD18 |
| | E-26 (2$^{nd}$ gen. IgE) | allergic asthma & rhinitis | IgE |
| IDEC | Zevalin (Rituxan + yttrium-90) | low grade of follicular, relapsed or refractory, CD20-positive, B-cell NHL and Rituximab-refractory NHL | CD20 |
| ImClone | Cetuximab + innotecan | refractory colorectal carcinoma | EGF receptor |
| | Cetuximab + cisplatin & radiation | newly diagnosed or recurrent head & neck cancer | EGF receptor |
| | Cetuximab + gemcitabine | newly diagnosed metastatic pancreatic carcinoma | EGF receptor |
| | Cetuximab + cisplatin + 5FU or Taxol | recurrent or metastatic head & neck cancer | EGF receptor |
| | Cetuximab + carboplatin + paclitaxel | newly diagnosed non-small cell lung carcinoma | EGF receptor |
| | Cetuximab + cisplatin | head & neck cancer (extensive incurable local-regional disease & distant metasteses) | EGF receptor |
| | Cetuximab + radiation | locally advanced head & neck carcinoma | EGF receptor |
| | BEC2 + Bacillus Calmette Guerin | small cell lung carcinoma | mimics ganglioside GD3 |
| | BEC2 + Bacillus Calmette Guerin | melanoma | mimics ganglioside GD3 |
| | IMC-1C11 | colorectal cancer with liver metasteses | VEGF-receptor |
| ImmonoGen | nuC242-DM1 | Colorectal, gastric, and pancreatic cancer | nuC242 |
| ImmunoMedics | LymphoCide | Non-Hodgkins lymphoma | CD22 |
| | LymphoCide Y-90 | Non-Hodgkins lymphoma | CD22 |
| | CEA-Cide | metastatic solid tumors | CEA |
| | CEA-Cide Y-90 | metastatic solid tumors | CEA |
| | CEA-Scan (Tc-99m-labeled arcitumomab) | colorectal cancer (radioimaging) | CEA |
| | CEA-Scan (Tc-99m-labeled arcitumomab) | Breast cancer (radioimaging) | CEA |
| | CEA-Scan (Tc-99m-labeled arcitumomab) | lung cancer (radioimaging) | CEA |
| | CEA-Scan (Tc-99m-labeled arcitumomab) | intraoperative tumors (radio imaging) | CEA |
| | LeukoScan (Tc-99m-labeled sulesomab) | soft tissue infection (radioimaging) | CEA |
| | LymphoScan (Tc-99m-labeled) | lymphomas (radioimaging) | CD22 |
| | AFP-Scan (Tc-99m-labeled) | liver 7 gem-cell cancers (radioimaging) | AFP |
| Intracel | HumaRAD-HN (+yttrium-90) | head & neck cancer | NA |
| | HumaSPECT | colorectal imaging | NA |
| Medarex | MDX-101 (CTLA-4) | Prostate and other cancers | CTLA-4 |
| | MDX-210 (her-2 overexpression) | Prostate cancer | HER-2 |
| | MDX-210/MAK | Cancer | HER-2 |
| MedImmune | Vitaxin | Cancer | $\alpha v \beta_3$ |
| Merck KGaA | MAb 425 | Various cancers | EGF receptor |
| | IS-IL-2 | Various cancers | Ep-CAM |

TABLE 1-continued

Therapeutic Antibodies That Can Be Optimized According to the Methods of the Invention

| Company | Product | Disease | Target |
| --- | --- | --- | --- |
| Millennium | Campath (alemtuzumab) | chronic lymphocytic leukemia | CD52 |
| NeoRx | CD20-streptavidin (+biotin-yttrium 90) | Non-Hodgkins lymphoma | CD20 |
| | Avidicin (albumin + NRLU13) | metastatic cancer | NA |
| Peregrine | Oncolym (+iodine-131) | Non-Hodgkins lymphoma | HLA-DR 10 beta |
| | Cotara (+iodine-131) | unresectable malignant glioma | DNA-associated proteins |
| Pharmacia Corporation | C215 (+staphylococcal enterotoxin) | pancreatic cancer | NA |
| | MAb, lung/kidney cancer | lung & kidney cancer | NA |
| | nacolomab tafenatox (C242 + staphylococcal enterotoxin) | colon & pancreatic cancer | NA |
| Protein Design Labs | Nuvion | T cell malignancies | CD3 |
| | SMART M195 | AML | CD33 |
| | SMART 1D10 | NHL | HLA-DR antigen |
| Titan | CEAVac | colorectal cancer, advanced | CEA |
| | TriGem | metastatic melanoma & small cell lung cancer | GD2-ganglioside |
| | TriAb | metastatic breast cancer | MUC-1 |
| Trilex | CEAVac | colorectal cancer, advanced | CEA |
| | TriGem | metastatic melanoma & small cell lung cancer | GD2-ganglioside |
| | TriAb | metastatic breast cancer | MUC-1 |
| Viventia Biotech | NovoMAb-G2 radiolabeled | Non-Hodgkins lymphoma | NA |
| | Monopharm C | colorectal & pancreatic carcinoma | SK-1 antigen |
| | GlioMAb-H (+gelonin toxin) | glioma, melanoma & neuroblastoma | NA |
| Xoma | Rituxan | Relapsed/refractory low-grade or follicular NHL | CD20 |
| | Rituxan | intermediate & high-grade NHL | CD20 |
| | ING-1 | adenomcarcinoma | Ep-CAM |

5.3 Other Methods for Use with the Invention

5.3.1 Use of the Dual Expression Vector System to Express Other Polypeptides and Fragments Thereof The dual expression vector system of the instant invention may be used to express any polypeptide of interest in a mammalian cell, and a fragment, preferably a soluble fragment, of said polypeptide in a bacterial cell, using the methods described for expressing antibodies disclosed herein. The polypeptide of interest should preferably be a membrane-bound or secreted polypeptide, and have a soluble domain which retains an activity which can be assayed when expressed and secreted into the periplasmic domain of a bacterial cell. Domains of interest may include, but are not limited to, DNA-binding domain, protein-protein interaction domains, a kinase domain or other enzymatic or functional protein domain.

The dual expression vector is constructed by inserting an intron into the signal sequence of the full length polypeptide. The intron is designed to comprise a bacterial promoter and a signal sequence overlapping the splice acceptor sequence and in frame with the coding region of the polypeptide of interest, so that transcription from the bacterial promoter directs expression of the domain of interest in a bacterial cell. Methods for construction of such sequences are described in detail in the example provided below.

The components of such a dual expression vector include: (a) a bacterial origin of replication, (b) a mammalian origin of replication, and (c) a mammalian promoter for expression operatively associated with a nucleotide sequence encoding said secreted or membrane-bound polypeptide, said nucleotide sequence comprising a mammalian signal sequence comprising at least one intron, said intron comprising a bacterial promoter and a bacterial signal sequence operatively associated with a sequence encoding said soluble domain of said polypeptide, such that said bacterial promoter and bacterial signal sequence direct expression and secretion of said soluble domain of said polypeptide into the periplasmic space in a bacterial cell and said mammalian promoter and said mammalian signal sequence directs expression and secretion of said polypeptide, wherein said promoter for expression in mammalian cells is operatively associated with said nucleotide sequence encoding said soluble domain of said polypeptide.

Examples of membrane-bound or secreted polypeptides of interest include, but are not limited to: cell surface receptors including, but not limited to, the erythropoietin receptor (Epo-R; Noguchi et al., 1991, Blood 78(10):2548–2556), the insulin receptor (InsR; Ebina et al., 1985, Cell 40:747–758; and Ullrich, 1985, Nature 313: 756–761), and the tumor necrosis factor alpha receptor (TNFαR; Gray et al., 1990, Proc. Natl. Acad. Sci. USA 87:7380–7384); members of the single transmembrane tyrosine receptor kinase (TRK)-like class of receptors (Ullrich & Schlessinger, 1990, Cell 61:203–12; Hunter & Cooper, 1985, Ann. Rev. Biochem. 54:897–930). This class includes: epidermal growth factor receptor family, including epidermal growth factor (EGF; Ullrich et al., Nature, 1984, 309:418–25; Schector et al., Nature 278:835–38), vaccinia growth factor (Brown et al., 1985, Nature 313:491–92), amphiregulin/schwannoma-derived growth factor (AR or SDGF; Schoyab et al., 1989, Science 243:1074–1076), heparin-binding EGF-like factor (HB-EGF; Higashiyama et al., 1991, Science 251:936–939), the neu differentiation factor (NDF; Wen et al. 1992, Cell, 69:559–72), and the heregulins (Holmes et al., 1992, Science 256:1205–10) such as Her2 (Coussens et al., 1985, Science 230:1132–39; and Santanta et al. 1994, Proc. Natl. Acad. Sci. USA 91:1711–1715); the insulin receptor family, including INSR, as above, and IRR; the platelet-derived growth factor (PDGF) receptor family, including α-PDGFR (Potts & Carrington, 1993, Dev. Dyn. 198: 14–21), β-PDGFR (Chi et al., 1997, Oncogene 15:1051–58), CSF1-R (e.g., Waterfield et al., 1983, Nature 304: 35–39), c-Kit stem cell factor receptor (Lemmon et al. 1997, J. Biol. Chem. 272:6311–6317); the fibroblast growth factor receptor (FGFR), including CEK2 (Pasquale, 1990, Proc. Natl. Acad. Sci. U.S.A. 87:5812–16); the TRK receptor family, including TRK and TRK-B; and the EPH/ECK receptor family including Elf-1 and Eck (Cheng & Flanagan, 1994, Cell 79:157–68; Lindberg & Hunter, 1990, Mol. Cell Biol. 10:6316–24); nerve growth factor receptor (Woo et al. 1998, Protein Sci. 7:1006–1016; Johnson et al., 1986, Cell 47:545–54); and insulin-like growth factor receptor (Ullrich et al., 1986, EMBO J. 5:2503–12; and Sepp-Lorenzino, 1998, Breast Cancer Res. Treat. 47:235–253). Other members of the TK-like family of receptors can also be utilized. See, e.g., van der Greer et al., 1997, Ann. Rev. Cell Biol. 10:251–337; and Herz et al. 1997, J. Recept. Signal Transduct. Res. 17:671–776, each of which is incorporated herein by reference in its entirety, and references therein.

In another embodiment, the polypeptide of interest may be a member of the 7-transmembrane class of receptors (e.g., the G-protein coupled class of receptor (GPCR), including the β3 adrenergic receptor (Emorine et al., 1989, Science 245: 1118–21; see Huang et al., 1997, J. Recept. Signal Transduct. Res. 17:599–607), dopamine receptor, e.g., dopamine D2 receptor (Wilkie et al., 1993, Genomics 18:175–184; Bunzow et al., 1988, Nature 336: 783–7) and the muscarinic acetylcholine receptor (see Strader et al., 1994, Ann. Rev. Biochem. 63:101–32, which are incorporated herein by reference in their entirety, and references cited therein); ion channels, including, but not limited to, the Kv1.3 potassium channel (Kath et al., 1997, in Annual Reports in Med. Chem., Hagmann, ed., 32:181–89) and the NHE1 and NHE2 Na+/H+ exchangers (Fafoumoux & Pouysseyur, 1994, J. Biol. Chem. 269:2589–96); voltage-gated ion channel family of receptors, such as the K+ sensitive channels and the Ca2+ sensitive channels (see, Hille, B. in "Ionic Channels of Excitable Membranes," 1992, Sinauer Associates, Sunderland, Mass.; Catterall, W. A., 1991, Science 253:1499–1500, which are incorporated herein by reference in their entirety, and references cited therein); members of the receptor protein-tyrosine phosphatase family, or R-PTPs, including but not limited to CD45 (or leukocyte-common antigen, LCA), R-PTPs α, β, γ, κ and others (see, e.g., Denu et al., 1996, Cell 87:361–64; Fashena and Zinn, 1995, Curr. Biol. 5:1367–69, each of which is incorporated herein by reference in its entirety; members of the cytokine receptor family: the IL-1 cytokine receptor family (IL-1α and IL-1β; see, e.g., Vigers et al. 1997, Nature 386:190–194); the class I cytokine family, particularly the growth hormone receptor subfamily of hematopoietic cytokine receptors, characterized by highly conserved cysteines involved in homodimerization (Watowich et al. Proc. Nat. Acad. Sci., 89:2140–44). This family includes not only EPO receptor (Noguchi et al., 1991, supra), but also growth hormone receptor (Cunningham et al., 1989, Science 243:1330), the prolactin receptor (Boutin et al., 1988, Cell 53:69), CSF, the granulocyte-colony stimulating factor receptor (Seto et al., 1992, J. Immunol. 148(1): 259–266), somatotropin receptor (Leung et al., 1987, Nature 330:537), glial-derived neurotrophic factor (GDNF) receptors, such as GFRα3 (Baloh et al. Proc. Natl. Acad. Sci. 95:5801–06), and many others (see Herz et al. 1997, supra); and the class II cytokine receptor (interferon) family members, in which ligand-binding may induce dimerization and activation through JAK kinases (Aguet et al., 1988, Cell 55:273–80; and Uze et al., 1990, Cell 60:225–234).

In another embodiment, the polypeptide of interest may be a member of the nuclear hormone receptor superfamily (see, e.g., Mangelsdorf et al., 1995, Cell 83:835–39, which is incorporated herein in its entirety, and references cited therein) including the steroid receptors (see Beato et al., 1995, Cell 83:851–57, which is incorporated here in its entirety, and references cited therein): glucocorticoid (Hollenberg et al., 1985, Nature, 318:635–41; see also Evans, 1989, Recent Prog. Horm. Res. 45:1–22, and references within, which are incorporated in their entirety), androgen (Tilley et al. Proc. Nat. Acad. Sci. U.S.A., 1989, 86:327–31), aldosterone, progesterone, and estrogen receptors (Greene et al, 1986, Nature 320:134–39; see also Tsai & O'Malley, 1994, Ann. Rev. Biochem. 63:451–86, which are incorporated herein their entirety, and references cited therein); and the heterodimeric receptors, including thyroxin, vitamin D, vitamin A, retinoid (RAR, RXR), prostinoid receptors (see Mangelsdorf & Evans, 1995, Cell 83:841–50 which is incorporated herein by reference in its entirety, and references cited therein) such as the hepatic nuclear factor HNF4 (Sladek et al., 1990, Genes Dev. 4:2353–65). Orphan receptors within these classes represent particularly interesting sequences which can be utilized as part of the methods of the invention for identifying ligands in that they represent a family of heterodimeric and homodimeric receptors whose putative ligands are not known.

In another embodiment, the polypeptide of interest may be a non-membrane non-secreted polypeptide, such as a nuclear transcription factor protein. Transcription factors include, but not limited to Fos/Jun (Bohmann et al., Science 238:1386–92; and Angel et al., 1988, Nature 332:166–71), C/EBP (Landshultz et al., 1988, Science, 240:1759–64), GCN4 (see, e.g., Agre et al., 1989, Science 246:922–926; see, also, the Example presented, below, Section 9); helix loop helix (HLH) domain proteins, for example Myc (Murre et al, 1989, Cell 56:777–783) and MyoD and other myogenic HLH proteins which require heterooligimerization with E12/E47-like proteins in vivo (Lasser et al., 1991, Cell 66:305–15), as well as other transcription factors well known in the art.

In addition to the proteins mentioned herein, a polypeptide of interest can comprise amino acid residues derived from any membrane-bound or secreted polypeptide polypeptide listed in public databases, such as, for example, the Swiss Protein Data Base (SWISS-PROT; see Bairoch & Apweiler, 1998, Nucl. Acids Res. 26:38–42).

5.3.2 Diagnostic Uses of Antibodies

Antibodies or Fab fragments produced by the vector system of the invention can be used to assay antigen levels in a biological sample using classical immunohistological methods as described herein or as known to those of skill in the art (e.g., see Jalkanen et al., 1985, J. Cell. Biol. 101: 976–985; and Jalkanen et al., 1987, J. Cell. Biol. 105: 3087–3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody or antibody fragment will then preferentially accumulate at the location of cells which contain the specific protein. In vivo tumor imaging is described in S. W. Burchiel et al., "Immmunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

6. EXAMPLES

6.1 Expression of Anti-CD16 Fab and IgG

To provide a basis for designing a dual expression vector for expression of Fab in *E. coli* and IgG in mammalian cells, the following preliminary studies were performed. Two vectors were constructed: first, a vector for expression of Fab molecules in *E. coli*, and second, a vector for expression of IgG in mammalian cells. Heavy chain and light chain cDNAs of either chimeric or humanized versions of an anti CD16 Mab were used to validate expression vectors.

In order to express Fab molecules in *E. coli*, a vector similar to that described by Barbas (Barbas et al., 1991, Proc. Natl. Acad. Sci. U.S.A. 88:7978 7982) was constructed, in which individual light chain (LC) sequences and VH CH1 (Fd) chain sequences were each fused to the pelB signal peptide coding sequence under the control of the lac promoter operator (lacPO). The Fd segment sequences also contained sequences encoding both a C terminal His tag for purification and an HSV epitope tag for identification.

This vector was used to secrete chimeric or humanized anti CD16 Fab into the periplasm of *E. coli* (strains BL21 or XL1 Blue) at approximately 1 mg/l. To test this material for binding activity, Fab was purified from periplasmic extracts and analyzed for the ability to bind the soluble portion of the CD16 receptor (sCD16) in a sandwich ELISA or to inhibit the binding of sCD16 to immune complexes. As shown in FIG. 1, the purified chimeric Fab migrates as a single 25 kd band on an SDS PAGE gel after reduction, or a single 50 kd band without reduction. This indicates that the product is disulfide-linked. On western blots, the bands are reactive with both anti LC and HSV tag antibody, indicating that both LC and Fd chains are present.

For expression of IgG, individual vectors were constructed in which sequences encoding the full length heavy chain (γ1) or light chain (K) genes were fused to a murine VH signal sequence and placed downstream from the CMVie promoter/enhancer in the vector pCI neo (Promega). The murine VH signal peptide coding region contains the naturally occurring intron and was found to be very reliable for secreting both light and heavy chain sequences from a number of antibodies. In contrast, cDNA sequences containing the signal peptide from the variable region being expressed for secretion resulted in more inconsistent results. Light and heavy chain plasmids for either chimeric or humanized anti CD16 were cotransfected into HEK 293 cells. Generally, 5 10 µg/ml are secreted into the culture medium after 3 days.

The material purified from both vectors was tested for binding either directly in ELISA, or purified and assayed for inhibition of binding of sCD16 to immune complexes formed between fluorescein BSA and a human IgG1 chimeric version of the anti fluorescein Mab 4 4 20. Inhibition of binding of sCD16 to immune complexes is shown in FIG. 2. The protocol used was as follows: A MaxiSorp immunoplate (Nunc F96) was coated with 500 ng/well of BSA FITC in carbonate buffer at 4° C. over night. The plate was blocked with 0.5% BSA in PBST for 30 minutes at room temperature. 50 ng/well of Ch4 4 20 (Human IgG1) was added to the plate and incubated at room temperature for 1 hour to form the immune complex. The purified Ch3G8Fab, Ch3G8 (as positive control), and human IgG1 (as negative control) were diluted in 0.5% BSA/PBST containing 0.5 ug/ml sCD16 G2 biotin to final concentrations indicated in the figure and added to the wells containing the immune complexes. The plate was then incubated for 2 hours incubation at room temperature. The binding of sCD16 G$_2$ biotin to the immune complex was detected by horseradish conjugated streptavidin (Pharmacia) in 1:5000 dilution. After 30 minutes incubation at room temperature, TMB (BioFX) was used as substrate for detection. Between the steps above, the plate was always washed 3 times with 1×PBS/0.1% Tween 20 (PBST). The plate was kept at room temperature for 5 10 minutes for color development. The reaction was stopped by 0.18M of sulfuric acid, and OD$_{450nm}$ was measured.

As shown in FIG. 3, this material was also active in direct binding to sCD16A. Soluble monomeric CD16 was captured onto an immunoplate that had been coated with the anti CD16 Mab LNK 16. After washing out unbound ligand, dilutions of chimeric Fab were added to the plate that was then incubated for 1 hr at room temperature. Bound Fab was then detected using a goat anti human Fab HRP conjugate followed by TMB development as described above. The results of this sCD16A binding assay are shown in FIG. 3.

6.1.1 Expression Vector for Expression of IgG Light and Heavy Chain in Mammalian Cells and Fab in *E. coli*

The following strategy was used for design and construction of a dual expression vector for expression and screening of Fab fragments in *E. coli* and of IgG in mammalian cells. In this embodiment of the invention, to obtain efficient expression and secretion in both systems according to the instant invention, two conditions were imposed: first, for *E. coli* expression and secretion, the signal peptides preceding the secreted polypeptide must be functional; and second, for mammalian expression and secretion, the message must be correctly spliced to join together the segments coding for the signal sequence. Since the region coding for the bacterial signal sequence overlaps with the mammalian splice acceptor site, the design of these two elements must be considered together.

The pelB signal peptide coding sequence from pET25b was used as a template for design and construction of this synthetic segment. This coding sequence was modified to maximize homology to a consensus 3' splice donor site, while retaining hydrophobic residues in the core of the signal peptide. This involved substituting leucine codons (CTC) for two alanine codons (GCC or GCT) to provide a pyrimidine stretch of adequate length for correct splicing. In addition, to provide a potential splicing branch point upstream from the pyrimidine stretch, an Ala codon (GCT) was changed to Ile (ATC). Finally, in the region shared by the prokaryotic and mammalian signal peptides, residues were chosen at positions −1 and −2 which would most likely retain functional activity in both systems. To predict whether modified prokaryotic signal peptides would still retain favorable splice cleavage sites, sequences were analyzed by SignalP program which uses neural network algorithm (Nielsen et al., 1997, Int. J. Neural Sys. 8, 581 599). The potential functionality of the splice sites was assessed using the Splice Site Prediction program at the Berkeley Drosophila Genome Project web site (see Reese et al., J. Comput. Biol., 1997, 4(3):311 23). This program also uses a neural network algorithm trained on human genes.

The plasmid vector pMGX115 contains a minigene coding for a humanized heavy chain in the mammalian expression vector pCI neo. In this minigene, the only intron is within the region coding for the signal peptide. The precise splice junction is located in the Gly codon at position −4 to the signal peptide cleavage site (see FIGS. 4A–B). The designed segment shown in FIG. 4A was introduced as follows: first, the lac promoter and operator (lacPO) sequence was obtained from pUC18 by PCR and introduced into pET25b as a BglII XbaI fragment, replacing the T7 promoter, generating pMGX102. The lacPO sequence together with the pelB signal sequence was then amplified by PCR using pMGX102 as template. This fragment was then placed between the two fragments from pMGX115 comprising the 5' exon of the signal sequence (including the 5' splice site) and the heavy chain (VH Cγ1), respectively, using overlapping PCR. The alterations in the signal sequences were introduced during this process by designing them into the overlapping PCR primers used to join the segment coding for the mature VH to the segment containing the lacPO pelB sequence. The resulting fragment was cloned into the expression vector pCI Neo, generating pMGX121.

To determine if the alteration of the intron, splice junction and signal peptide would affect expression and secretion, expression of pMGX121 was examined in HEK 293 cells. No deleterious effect was seen on expression, as measured in an ELISA in which human IgG is captured using an anti human Fc antibody and detected using an anti human heavy+light chain HRP conjugate.

In order to provide a stop codon for *E. coli* expression of Fd (VH CH1 fragment), a second intron was introduced into pMGX121 between CH1 and the hinge region, generating pMGX578 (see FIG. 4B). The intron from the native human γ1 gene was amplified from genomic DNA by a nested PCR and joined to the other segments by overlapping PCR. Site directed mutagenesis was then performed to introduce a stop codon near the beginning of the intron. Again, the sequence was designed so as not to interfere with splicing, and the retention of the splice site sequence was examined using the program described above. The resulting plasmid, pMGX579, was then sequenced and expression in HEK 293 cells, when co transfected with LC (light chain) expression plasmid, was confirmed.

To generate a similar LC expression plasmid, the signal intron containing the lacPO pelB sequences from pMGX121 was combined with the humanized light chain coding sequence by an overlapping PCR procedure and this fragment was cloned into pMGX581, which is identical to pMGX579 except that AscI sites have been introduced at the 5' end of the CMVie promoter and at the 3' end of the SV40 polyA site to allow the entire expression cassette to be excised. This plasmid was named pMGX582.

Expression of LC from this plasmid was tested as follows. *E. coli* strain XL 10 gold, harboring either pMGX506 or pMGX582 (LC), was induced with 0.5 mM IPTG. Three hours later, cells were collected and the periplasmic fraction was isolated. This material was diluted ½ and ¹⁄₁₀ and applied to microtiter plates which had been coated with goat anti human Fab (Jackson). After incubating at room temperature for approximately one hour, the unbound material was washed out and the bound light chain (LC) was detected using HRP conjugated goat anti human LC (Biosource, Inc.). After one hour incubation at room temperature, the plate was developed using TMB reagent and color development stopped after approximately 10 minutes using 0.18 M H2SO4. The results, shown in FIG. 6, confirmed expression of LC in *E. coli* from this plasmid. Especially significant was the apparent secretion of the LC into the *E. coli* periplasm, indicating that the signal sequence was functional. Expression of IgG after cotransfection of this plasmid with heavy chain (HC) expression plasmid pMGX115 was also demonstrated.

The plasmid pMGX583 was constructed in order to assess the expression of Fab in *E. coli* and IgG in mammalian cells. pMGX583 contains both HC and LC expression cassettes, each with the lacPO pelB intronic sequence. To construct pMGX583, the entire expression cassette, CMvie lacPO pelB LC SV40pA was excised by digestion with AscI and ligated into pMGX580 (which is identical to pMGX579 except that the AscI site was introduced into the 5' end of CMvie promoter). The expression of IgG from this plasmid has been confirmed by transfection into HEK 293 cell and followed by goat anti human Fc antibody captured ELISA. The IgG was purified by protein G chromatography and analyzed in SDS PAGE and Western blot. Coomassie Blue staining and western blot of purified IgG expressed from pMGX583 in HEK 293 cells. Protein was analyzed in SDS PAGE under reduction condition. In the Western blot, 1:5000 dilution of goat anti human IgG(Fab')2 AP conjugated (Jackson) was used and developed by Chromogen. The results are shown in FIG. 7.

Expression of Fab in *E. coli* (strains BL21 or XL1-blue) from pMGX583 was also evaluated. Since pMGX121-derived plasmids do not contain a copy of the lac repressor gene, the plasmid pLac1 (Novagen) was provided. pLac1 is a chloramphenicol resistant plasmid that encodes the lac repressor protein and has a p 1 Sa origin of replication which is compatible with pMGX121-derived vectors. pLac1 and pMGX583 were contransformed into the E. coli, and colonies selected with ampicillin and chloramphenicol. Transformants were grown up and induced with 1 mM IPTG as described below. The Fab from a periplasmic extract was captured by sCD16A and detected by goat anti human F(ab')2 HRP conjugated (Jackson), as shown in FIG. 8. The same amount of periplasmic extract from un induced and induced (IPTG, 1 mM) were used. Commercially available human IgG1 was used as control. Serial dilutions of purified ch3G8Fab from the previous construct, as shown in FIG. 2, was used as a standard. The estimated expression of Fab in periplasmic from pMGX583 plasmid is approximately 10 ng per ml of culture.

TABLE 2

Expression of IgG, LC, and Fab

| HC plasmid | LC plasmid | IgG expression in HEK-293 | Fab Expression in E. coli | LC expression in E. coli |
|---|---|---|---|---|
| pMGX121 | pMGX208 | + | ND | ND |
| pMGX578 | pMGX208 | + | ND | ND |
| pMGX579 | pMGX208 | + | ND | ND |
| pMGX115 | pMGX582 | + | ND | + |
| pMGX583 | same | + | + | + |

The preliminary work described above has demonstrated that prokaryotic transcription and translation signals can be introduced into the signal intron of an IgG heavy chain or light chain construct without reducing expression or secretion in mammalian cells.

Enough Fab is prepared from E. coli obtain N terminal sequence of the LC and Fd fragment. Mass spectroscopic analysis is performed on the intact Fab as well as the reduced and alkylated chains. A similar analysis is performed on Mab produced transiently in mammalian cells.

To increase the Fab secretion level to the periplasm in bacteria, several modifications of peptide in the bacterial signal sequence region have been designed and constructed. The amino acids at a number of positions were reverted to that contained in the pelB sequence as shown below.

```
PelB       MKYLLPTAAAGLLLLAAQPAMA    (SEQ ID NO: 13)

Initial    MKYLLPTAAIGLLLLLLTGVHA    (SEQ ID NO: 14)
sequence:

>seq2      MKYLLPTAAIGLLLLLLTGAHA    (SEQ ID NO: 15)

>seq3      MKYLLPTAAIGLLLLLLTGAMA    (SEQ ID NO: 16)

>seq4      MKYLLPTAAIGLLLLAATGVHA    (SEQ ID NO: 17)

>seq5      MKYLLPTAAIGLLLLLLTGVAHA   (SEQ ID NO: 18)

>seq6      MKYLLPTAAIGLLLLAATGAHA    (SEQ ID NO: 19)

>seq7      MKYLLPTAAIGLLLLAATGAMA    (SEQ ID NO: 20)

>seq8      MKYLLPTAAAGLLLLLLTGVHA    (SEQ ID NO: 21)
```

To predict whether modified signal peptides still retain favorable splice cleavage sites, sequences were analyzed by SignalP program. The individual modifications have been made and are tested in the both bacterial and mammalian cell systems. Mutations have been introduced in the intron of the HC/Fd gene in a vector also containing the LC cDNA with the original lacZ pelB segment from pMGX102 (i.e., wt pelB). In this way, the contribution of the mutations to increased secretion can be assessed by analysis of antigen binding by the secreted Fab in periplasmic extracts. For mammalian expression, the LC gene can be co transfected on a second plasmid. Combinations of mutations will then be made as dictated by the results of the initial analysis.

Codon usage has also been shown to influence the successful cleavage of signal peptides. To exploit this possibility, and to capture any unpredictable variation which could promote improved secretion, libraries of E. coli mutants are screened with random variability introduced into this region. These are constructed with degenerate or doped oligonucleotides and screened by both a colony lift method and by high throughput screening of periplasmic extracts. The incorporation of epitope tags is particularly useful for this screening.

Materials and Methods. Vectors are modified to introduce new genetic elements using basic cloning methods, overlapping PCR methods and site directed mutagenesis (Quick change kit, Stratagene). All new constructs are subjected to DNA sequencing to confirm that no unwanted mutations were introduced into the sequences during construction. To assure the stability of the plasmids in E. coli, the recipient strains are lacIq+ and, if necessary, lacI is provided on a compatible plasmid or on the construct itself. In addition, plasmid-bearing cells are grown in rich medium or with glucose present prior to induction, in order to prevent induction of the lac promoter by CRP. The following protocol is followed for induction of expression. Cells are grown overnight at 30° C. from a single colony in L broth (10 g of Bactotryptone, 5 g yeast extract, 10 g NaCl per liter). The overnight culture is diluted 1/100 in LB and the culture grown at 30° C. to an OD600 of approximately 0.2. At this point, the culture is divided into three flasks and two are induced with either 0.1, or 1 mM IPTG respectively (from a 100 mM stock). The other flask will serve as a uniniduced control. Three hours after induction, cells are harvested and the periplasmic fraction isolated by osmotic shock. The resulting fraction is assayed for the presence of Fab by ELISA and by western blot. In the ELISA assay, Fab is captured with Goat anti human light chain and detected with mouse anti Fd followed by a rabbit anti mouse HRP conjugate. Purified Fab, either that described in the preliminary results section or obtained from a vendor, is used to generate a standard curve for the assay.

For detection of the retaining function of the Fab, a captured antigen binding ELISA assay was applied. The purified Fab from periplasmic or unpurified periplasmic extraction was captured by sCD16 and detected by goat anti human F(ab')2 HRP conjugated antibody (Jackson). The commercial purified human IgG1 was used as a negative control.

Analysis of expression from mammalian cells. For measuring the expression and secretion level in mammalian cells, individual constructs, as indicated in Table 1, were expressed transiently in human embryonic kidney 293 cells (HEK 293) by transfection with LipofectAMINE 2000

Reagent (Invitrogen). The day before transfection, cells were plated on poly D lysine precoated dishes (Becton Dickinson) at 5×10⁶ cells/dish (100 mm). For each dish of cells, 18 µl of total DNA was diluted into 1.4 ml of OPTIMEM I Reduced Serum Medium (Invitrogen). 54 µl of LipofectAMINE Reagent (Invitrogen) was diluted into 1.4 ml of OPTI MEM I Reduced Serum Medium and incubated for 5 mins at room temperature. Diluted DNA and LIPOFECTAMINE Reagent were then combined and incubated at room temperature for 20 mins to allow complexes to form. The DNA LipofectAMINE Reagent complexes were directly added to the cells. The cells were incubated at 37° C. in a $CO_2$ (5%) incubator for 72 hrs to allow the recombinant IgG secretion to the medium. The conditional medium is assayed for the expression level of IgG by ELISA and Western Blot. In the ELISA assay, IgG (in the conditional medium) is captured with goat anti human Fc antibody (Jackson) and detected with goat anti human IgG (light+heavy) HRP conjugate. Purified human IgG1 from commercial was used for the standard curve.

6.2 Phage Display and Screening Methods

Screening methods for the exploitation of this vector involving both *E. coli* expressed Fabs and mammalian expressed IgGs are encompassed by the present invention. A modified version of pET25b is utilized to express Fab. In that case, the LC was not epitope-tagged and the Fd chain was expressed with a C terminal HSV tag followed by a hexahistidine tag for purification. This sequence is incorporated into the construct in two ways. First, an amber (TAG) stop codon is used instead of the ochre codon currently present (TAA). This allows read through translation in a suppressor (supE) strain of *E. coli*. Such a construct is particularly useful for phage display and this strategy has been used previously (Hoogenboom et al., 1991, Nucleic Acids Res. 19: 4133 4137). The amber codon would be suppressed in a strain such as XL1 blue (supE44+), allowing for incorporation of Fab into phage particles, but not in BL21 (sup), the favored strain for Fab expression.

```
CH1 intron
Asp Lys Arg Val gly glu        (SEQ ID NO: 23)
arg pro Stop

GAC AAG AGA GTT GGT GAG        (SEQ ID NO: 22)
AGG CCA TAA . . .

Asp Lys Arg Val gly glu        (SEQ ID NO: 25)
arg pro Amb Stop

GAC AAG AGA GTT GGT GAG        (SEQ ID NO: 24)
AGG CCA TGA +
HSVtag-His₆-TAA
```

Alternatively, a restriction site, such as HindIII as shown below, is inserted for subsequent addition of epitope and/or affinity tags.

```
CH1 intron
Asp Lys Arg Val gly glu        (SEQ ID NO: 23)
arg pro Stop

GAC AAG AGA GTT GGT GAG        (SEQ ID NO: 22)
AGG CCA TAA . . .

Asp Lys Arg Val gly glu        (SEQ ID NO: 27)
lys leu Stop
```

```
GAC AAG AGA GTT GGT GAG        (SEQ ID NO: 26)
AAG CTT +
HSVtag-His6-TAA HinDIII
```

Genes III and VIII from filamentous phage. Fusions to phage coat (gene VIII) or attachment (gene III) protein coding regions have been most widely used in phage display. Fusions of the Fd (VH CH1) gene segment to each of these gene segments are constructed. The genes are isolated by PCR from the fd tet phage. For the gene III fusion, the segment from P198 to S406 of the gene is used. The fusion is constructed such that the gene III segment replaces the hexahistadine tag in the above vector, retaining the HSV epitope tag between CH1 and the gene III segment. A similar construct is made with a segment of the gene VIII gene for multivalent display of Fab.

Phage analysis Standard conditions are used for phage preparation and analysis. Phagemids are grown in *E. coli* strain XL1 Blue. Log phase cultures grown at 37° C. are infected with helper phage VCSM13 and cultured for approximately 12 hr. Phage are isolated from the culture supernatant by PEG/NaCl precipitation and the resulting pellet resuspended in TBS15. A portion of the phage are analyzed by ELISA for the presence Fab on the surface. In addition bound phage are eluted from the immunoplate to determine the binding of the phage to surface bound sCD16 Ig or an identical preparation of sCD32 Ig. Phage bearing active anti CD16 Fab should bind to the former molecule but not the latter. Preincubation with sCD16 Ig in solution is used to block binding. Elution of the phagemid from the plates is performed using a low pH solution (glycine HCl pH 2.2) followed by neutralization. Phagemids are plated with XL1 Blue on ampicillin containing plates for determination of titers.

(Fab')2

For the expression of Fab', the following modification is tested after introduction of the hinge CH1 intron at the appropriate site into the HC minigene (SEQ ID NOs:28–31).

```
P   P   C   P   G   K   P   A

CCA CCG TGC CCA GGT AAG CCA GCC Human C Gamma1 CH1-

Hinge SD

MA G|GT RAG T

CCA CCG TGC CCA GGT AAG CTT TAG Stop codon for Fab'

P   P   C   P   G   K   L   Amb
```

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated by reference herein in their entireties for all purposes.

What is claimed:

1. A vector for expression of a heavy chain or light chain of an IgG in mammalian cells and a Fab fragment portion of a heavy chain or light chain in *E. coli*, said vector comprising:
   (a) a bacterial origin of replication;
   (b) a mammalian origin of replication;
   (c) a mammalian promoter and/or enhancer sequence; and
   (d) a nucleotide sequence encoding said heavy chain or said light chain; said nucleotide sequence comprising:
      (i) a mammalian signal sequence comprising a first intron, said first intron comprising a bacterial promoter and a bacterial signal sequence operatively associated with a sequence encoding the Fab domain of said heavy chain or said light chain, such that said bacterial promoter and bacterial signal sequence direct expression and secretion into the periplasmic space of said Fab domain of said heavy chain or said light chain in a bacterial cell and said mammalian promoter and said mammalian signal sequence directs expression and secretion of said heavy chain or said light chain in a mammalian cell; and
      (ii) when said vector encodes said heavy chain, a second intron between the CH1 and the hinge region of said heavy chain sequence, said second intron comprising a stop codon,
   wherein said promoter for expression in mammalian cells is operatively associated with said nucleotide sequence encoding said heavy chain or said light chain.

2. The vector of claim 1, wherein said bacterial promoter comprises a lacPO sequence.

3. The vector of claim 1, wherein said heavy chain or said light chain is a human heavy chain or light chain sequence or humanized heavy chain or light chain sequence.

4. The vector of claim 1, wherein said heavy chain or said light chain is a chimeric heavy chain or light chain sequence.

5. The vector of claim 1, wherein said bacterial signal sequence is a pelB signal sequence.

6. The vector of claim 1, wherein said promoter for expression in mammalian cells is a CMV promoter.

7. The vector of claim 1, wherein said vector encodes both heavy and light chains.

8. The vector of claim 1 wherein said light chain sequence is genetically modified to comprise a sequence encoding an epitope tag or affinity label.

9. The vector of claim 8 wherein the epitope tag is an HSV tag at the C-terminal of the Fd chain.

10. The vector of claim 8 wherein the affinity tag is a hexahistadine tag at the C-terminal of the Fd chain.

11. A bacterial cell comprising the vector of claim 1.

12. The bacterial cell of claim 11 which is an *E. coli* cell.

13. A mammalian cell comprising the vector of claim 1.

14. The mammalian cell of claim 13 which is a human cell or a murine cell.

15. The mammalian cell of claim 13 which is a myeloma cell, a CHO cell, or a HEK cell.

16. The cell of claim 11 or 13 wherein the vector comprises a nucleotide sequence for both heavy chain and light chains.

17. A cell which expresses a heavy chain and comprises the vector of claim 1 which comprises a light chain nucleotide sequence.

18. A cell which expresses a light chain and comprises the vector of claim 1 which comprises a heavy chain nucleotide sequence.

19. The vector of claim 1 wherein sequences encoding an Fd (VH CH1) segment of the IgG gene are operatively linked to sequences encoding an fd phage gene VIII protein coding region such that, when the vector is expressed in bacterial cells, and fd phage gene VIII fusion is produced.

20. The vector of claim 1 wherein sequences encoding an Fd (VH CH1) segment of the IgG gene are operatively linked to sequences encoding an fd phage gene III protein coding region such that, when the vector is expressed in bacterial cells, and fd phage gene III fusion is produced.

21. A composition comprising a plurality of bacterial cells (a) expressing Fab polypeptides and (b) comprising the vector of claim 1.

22. A composition comprising a plurality of bacterial cells comprising:

(a) the vector of claim 1 and (b) filamentous phage.

23. The composition of claim 21 or 22 wherein the bacterial cells are *E. coli* cells.

24. The composition of claim 22 wherein the filamentous phage is a helper phage.

25. The composition of claim 24 wherein the helper phage is selected from the group consisting of fd and M13.

26. The composition of claim 24 wherein the helper phage is fd.

27. The composition of claim 24 wherein the helper phage is M13.

* * * * *

SEQUENCE LISTING

<160> NUMBER OF SEQ ID NOS: 31

<210> SEQ ID NO 1
<211> LENGTH: 9
<212> TYPE: PRT
<213> ORGANISM: Influenza virus

<400> SEQUENCE: 1

Tyr Pro Tyr Asp Val Pro Asp Tyr Ala
1               5

<210> SEQ ID NO 2
<211> LENGTH: 10
<212> TYPE: PRT
<213> ORGANISM: Homo sapiens

<400> SEQUENCE: 2

Glu Gln Lys Leu Ile Ser Glu Glu Asp Leu
1               5                   10

<210> SEQ ID NO 3
<211> LENGTH: 6
<212> TYPE: PRT
<213> ORGANISM: Bluetongue virus

<400> SEQUENCE: 3

Gln Tyr Pro Ala Leu Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Description of artificial sequence:   FLAG
      protein

<400> SEQUENCE: 4

Asp Tyr Lys Asp Asp Asp Asp Lys
1               5

<210> SEQ ID NO 5
<211> LENGTH: 9
<212> TYPE: PRT
<213> ORGANISM: Streptococcus sp.

<400> SEQUENCE: 5

Ala Trp Arg His Pro Gln Phe Gly Gly
1               5

<210> SEQ ID NO 6
<211> LENGTH: 331
<212> TYPE: DNA
<213> ORGANISM: Artificial Sequence
<220> FEATURE:
<223> OTHER INFORMATION: Description of artificial sequence:   Mammalian
      and bacteria signal peptide hybrid
<220> FEATURE:
<221> NAME/KEY: exon
<222> LOCATION: (1)..(45)
<220> FEATURE:
<221> NAME/KEY: CDS
<222> LOCATION: (251)..(304)
<220> FEATURE:
<221> NAME/KEY: exon
<222> LOCATION: (305)..(331)

<400> SEQUENCE: 6

```
atg gga tgg agc tgt atc atc ctc ttc ttg gta gca aca gct aca       45
Met Gly Trp Ser Cys Ile Ile Leu Phe Leu Val Ala Thr Ala Thr
1               5                   10                  15 ggtaagggc tcacagtagc aggcttgagg tctggacata tatatgggtg acaagatctc  105
gcaacgcaat taatgtgagt tagctcactc attaggcacc ccaggcttta cactttatgc 165 ttccggctcg tatgttgtgt ggaattgtga gcggataaca atttctagaa ataattttgt 225 ttaactttaa gaaggagata tacat atg aaa tac ctg ctg cca acc gct gcg   277
                             Met Lys Tyr Leu Leu Pro Thr Ala Ala
                                                         20 atc ggt ctc ctt ctc ctc ctc ctc aca ggt gtc cac gca cag gtt acc  325
Ile Gly Leu Leu Leu Leu Leu Leu Thr Gly Val His Ala Gln Val Thr
25              30                  35                  40 ctg aga                                                          331
Leu Arg
```

<210> SEQ ID NO 7
<211> LENGTH: 18
<212> TYPE: PRT
<213> ORGANISM: Artificial Sequence
<220> FEATURE:
<223> OTHER INFORMATION: Description of artificial sequence: Mammalian
    and bacteria signal peptide hybrid

<400> SEQUENCE: 7

```
Met Lys Tyr Leu Leu Pro Thr Ala Ala Ile Gly Leu Leu Leu Leu Leu
1               5                   10                  15

Leu Thr
```

<210> SEQ ID NO 8
<211> LENGTH: 24
<212> TYPE: PRT
<213> ORGANISM: Artificial Sequence
<220> FEATURE:
<223> OTHER INFORMATION: Description of artificial sequence: Mammalian
    and bacteria signal peptide hybrid

<400> SEQUENCE: 8

```
Met Gly Trp Ser Cys Ile Ile Leu Phe Leu Val Ala Thr Ala Thr Gly
1               5                   10                  15

Val His Ala Gln Val Thr Leu Arg
                20
```

<210> SEQ ID NO 9
<211> LENGTH: 27
<212> TYPE: DNA
<213> ORGANISM: Artificial Sequence
<220> FEATURE:
<223> OTHER INFORMATION: Description of artificial sequence: Mammalian
    and bacteria signal peptide hybrid
<220> FEATURE:
<221> NAME/KEY: CDS
<222> LOCATION: (1)..(27)

<400> SEQUENCE: 9

```
gac aag aga gtt ggt gag agg caa gca                               27
Asp Lys Arg Val Gly Glu Arg Gln Ala
1               5
```

<210> SEQ ID NO 10
<211> LENGTH: 9
<212> TYPE: PRT

```
<213> ORGANISM: Artificial Sequence
<220> FEATURE:
<223> OTHER INFORMATION: Description of artificial sequence:  Mammalian
      and bacteria signal peptide hybrid

<400> SEQUENCE: 10

Asp Lys Arg Val Gly Glu Arg Gln Ala
1               5

<210> SEQ ID NO 11
<211> LENGTH: 27
<212> TYPE: DNA
<213> ORGANISM: Artificial Sequence
<220> FEATURE:
<223> OTHER INFORMATION: Description of artificial sequence:  Mammalian
      and bacteria signal peptide hybrid
<220> FEATURE:
<221> NAME/KEY: CDS
<222> LOCATION: (1)..(27)

<400> SEQUENCE: 11 gac aag aga gtt ggt gag agg cca taa                               27
Asp Lys Arg Val Gly Glu Arg Pro
1               5

<210> SEQ ID NO 12
<211> LENGTH: 8
<212> TYPE: PRT
<213> ORGANISM: Artificial Sequence
<220> FEATURE:
<223> OTHER INFORMATION: Description of artificial sequence:  Mammalian
      and bacteria signal peptide hybrid

<400> SEQUENCE: 12

Asp Lys Arg Val Gly Glu Arg Pro
1               5

<210> SEQ ID NO 13
<211> LENGTH: 22
<212> TYPE: PRT
<213> ORGANISM: Artificial Sequence
<220> FEATURE:
<223> OTHER INFORMATION: Description of artificial sequence: Modified
      signal peptide

<400> SEQUENCE: 13

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 14
<211> LENGTH: 22
<212> TYPE: PRT
<213> ORGANISM: Artificial Sequence
<220> FEATURE:
<223> OTHER INFORMATION: Description of artificial sequence: Modified
      signal peptide

<400> SEQUENCE: 14

Met Lys Tyr Leu Leu Pro Thr Ala Ala Ile Gly Leu Leu Leu Leu Leu
1               5                   10                  15

Leu Thr Gly Val His Ala
            20

<210> SEQ ID NO 15
<211> LENGTH: 22
```

```
<212> TYPE: PRT
<213> ORGANISM: Artificial Sequence
<220> FEATURE:
<223> OTHER INFORMATION: Description of artificial sequence: Modified
      signal peptide

<400> SEQUENCE: 15

Met Lys Tyr Leu Leu Pro Thr Ala Ala Ile Gly Leu Leu Leu Leu
1               5                  10                  15

Leu Thr Gly Ala His Ala
            20

<210> SEQ ID NO 16
<211> LENGTH: 22
<212> TYPE: PRT
<213> ORGANISM: Artificial Sequence
<220> FEATURE:
<223> OTHER INFORMATION: Description of artificial sequence: Modified
      signal peptide

<400> SEQUENCE: 16

Met Lys Tyr Leu Leu Pro Thr Ala Ala Ile Gly Leu Leu Leu Leu
1               5                  10                  15

Leu Thr Gly Ala Met Ala
            20

<210> SEQ ID NO 17
<211> LENGTH: 22
<212> TYPE: PRT
<213> ORGANISM: Artificial Sequence
<220> FEATURE:
<223> OTHER INFORMATION: Description of artificial sequence: Modified
      signal peptide

<400> SEQUENCE: 17

Met Lys Tyr Leu Leu Pro Thr Ala Ala Ile Gly Leu Leu Leu Ala
1               5                  10                  15

Ala Thr Gly Val His Ala
            20

<210> SEQ ID NO 18
<211> LENGTH: 23
<212> TYPE: PRT
<213> ORGANISM: Artificial Sequence
<220> FEATURE:
<223> OTHER INFORMATION: Description of artificial sequence: Modified
      signal peptide

<400> SEQUENCE: 18

Met Lys Tyr Leu Leu Pro Thr Ala Ala Ile Gly Leu Leu Leu Leu
1               5                  10                  15

Leu Thr Gly Val Ala His Ala
            20

<210> SEQ ID NO 19
<211> LENGTH: 22
<212> TYPE: PRT
<213> ORGANISM: Artificial Sequence
<220> FEATURE:
<223> OTHER INFORMATION: Description of artificial sequence: Modified
      signal peptide

<400> SEQUENCE: 19

Met Lys Tyr Leu Leu Pro Thr Ala Ala Ile Gly Leu Leu Leu Ala
1               5                  10                  15
```

```
Ala Thr Gly Ala His Ala
            20

<210> SEQ ID NO 20
<211> LENGTH: 22
<212> TYPE: PRT
<213> ORGANISM: Artificial Sequence
<220> FEATURE:
<223> OTHER INFORMATION: Description of artificial sequence: Modified
      signal peptide

<400> SEQUENCE: 20

Met Lys Tyr Leu Leu Pro Thr Ala Ala Ile Gly Leu Leu Leu Leu Ala
1               5                   10                  15

Ala Thr Gly Ala Met Ala
            20

<210> SEQ ID NO 21
<211> LENGTH: 22
<212> TYPE: PRT
<213> ORGANISM: Artificial Sequence
<220> FEATURE:
<223> OTHER INFORMATION: Description of artificial sequence: Modified
      signal peptide

<400> SEQUENCE: 21

Met Lys Tyr Leu Leu Pro Thr Ala Ala Ala Gly Leu Leu Leu Leu Leu
1               5                   10                  15

Leu Thr Gly Val His Ala
            20

<210> SEQ ID NO 22
<211> LENGTH: 27
<212> TYPE: DNA
<213> ORGANISM: Artificial Sequence
<220> FEATURE:
<223> OTHER INFORMATION: Description of artificial sequence:  Construct
      for screening tag
<220> FEATURE:
<221> NAME/KEY: CDS
<222> LOCATION: (1)..(27)

<400> SEQUENCE: 22 gac aag aga gtt ggt gag agg cca taa                            27
Asp Lys Arg Val Gly Glu Arg Pro
1               5

<210> SEQ ID NO 23
<211> LENGTH: 8
<212> TYPE: PRT
<213> ORGANISM: Artificial Sequence
<220> FEATURE:
<223> OTHER INFORMATION: Description of artificial sequence:  Construct
      for screening tag

<400> SEQUENCE: 23

Asp Lys Arg Val Gly Glu Arg Pro
1               5

<210> SEQ ID NO 24
<211> LENGTH: 27
<212> TYPE: DNA
<213> ORGANISM: Artificial Sequence
<220> FEATURE:
<223> OTHER INFORMATION: Description of artificial sequence:  Construct
      for screening tag
<220> FEATURE:
<221> NAME/KEY: CDS
```

```
<222> LOCATION: (1)..(27)

<400> SEQUENCE: 24 gac aag aga gtt ggt gag agg cca tga                              27
Asp Lys Arg Val Gly Glu Arg Pro
1               5

<210> SEQ ID NO 25
<211> LENGTH: 8
<212> TYPE: PRT
<213> ORGANISM: Artificial Sequence
<220> FEATURE:
<223> OTHER INFORMATION: Description of artificial sequence:  Construct
      for screening tag

<400> SEQUENCE: 25

Asp Lys Arg Val Gly Glu Arg Pro
1               5

<210> SEQ ID NO 26
<211> LENGTH: 27
<212> TYPE: DNA
<213> ORGANISM: Artificial Sequence
<220> FEATURE:
<223> OTHER INFORMATION: Description of artificial sequence:  Construct
      for screening tag
<220> FEATURE:
<221> NAME/KEY: CDS
<222> LOCATION: (1)..(27)

<400> SEQUENCE: 26 gac aag aga gtt ggt gag agg cca taa                              27
Asp Lys Arg Val Gly Glu Arg Pro
1               5

<210> SEQ ID NO 27
<211> LENGTH: 8
<212> TYPE: PRT
<213> ORGANISM: Artificial Sequence
<220> FEATURE:
<223> OTHER INFORMATION: Description of artificial sequence:  Construct
      for screening tag

<400> SEQUENCE: 27

Asp Lys Arg Val Gly Glu Arg Pro
1               5

<210> SEQ ID NO 28
<211> LENGTH: 24
<212> TYPE: DNA
<213> ORGANISM: Artificial Sequence
<220> FEATURE:
<223> OTHER INFORMATION: Description of artificial sequence:  Construct
      for insertion of the hinge CH1 intron
<220> FEATURE:
<221> NAME/KEY: CDS
<222> LOCATION: (1)..(24)

<400> SEQUENCE: 28 cca ccg tgc cca ggt aag cca gcc                                  24
Pro Pro Cys Pro Gly Lys Pro Ala
1               5

<210> SEQ ID NO 29
<211> LENGTH: 8
<212> TYPE: PRT
<213> ORGANISM: Artificial Sequence
<220> FEATURE:
<223> OTHER INFORMATION: Description of artificial sequence:  Construct
```

```
                for insertion of the hinge CH1 intron

<400> SEQUENCE: 29

Pro Pro Cys Pro Gly Lys Pro Ala
1               5

<210> SEQ ID NO 30
<211> LENGTH: 24
<212> TYPE: DNA
<213> ORGANISM: Artificial Sequence
<220> FEATURE:
<223> OTHER INFORMATION: Description of artificial sequence:  Construct
      for insertion of the hinge CH1 intron
<220> FEATURE:
<221> NAME/KEY: CDS
<222> LOCATION: (1)..(24)

<400> SEQUENCE: 30 cca ccg tgc cca ggt aag ctt tag                                       24
Pro Pro Cys Pro Gly Lys Leu
1               5

<210> SEQ ID NO 31
<211> LENGTH: 7
<212> TYPE: PRT
<213> ORGANISM: Artificial Sequence
<220> FEATURE:
<223> OTHER INFORMATION: Description of artificial sequence:  Construct
      for insertion of the hinge CH1 intron

<400> SEQUENCE: 31

Pro Pro Cys Pro Gly Lys Leu
1               5
```